United States Patent
Wogoman et al.

(10) Patent No.: US 11,957,591 B2
(45) Date of Patent: Apr. 16, 2024

(54) ORTHOPAEDIC KNEE PROSTHESIS SYSTEM AND METHODS FOR USING SAME

(71) Applicant: Depuy Ireland Unlimited Company, Ringaskiddy (IE)

(72) Inventors: Thomas E. Wogoman, Warsaw, IN (US); Mark A. Heldreth, Warsaw, IN (US); Amitkumar M. Mane, South Whitley, IN (US); Michael J. Rock, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 171 days.

(21) Appl. No.: 17/015,482

(22) Filed: Sep. 9, 2020

(65) Prior Publication Data
US 2021/0068967 A1 Mar. 11, 2021

Related U.S. Application Data

(60) Provisional application No. 62/898,256, filed on Sep. 10, 2019.

(51) Int. Cl.
| | |
|---|---|
| A61F 2/00 | (2006.01) |
| A61B 17/15 | (2006.01) |
| A61B 17/58 | (2006.01) |
| A61B 17/60 | (2006.01) |
| A61F 2/30 | (2006.01) |
| A61F 2/38 | (2006.01) |
| A61F 2/46 | (2006.01) |

(52) U.S. Cl.
CPC ........ *A61F 2/3859* (2013.01); *A61F 2/30771* (2013.01); *A61F 2/3868* (2013.01); *A61F 2/389* (2013.01); *A61F 2/461* (2013.01); *A61F 2/4684* (2013.01); *A61F 2002/30845* (2013.01); *A61F 2002/3863* (2013.01)

(58) Field of Classification Search
None
See application file for complete search history.

(56) References Cited

U.S. PATENT DOCUMENTS

| | | |
|---|---|---|
| 3,748,662 A | 7/1973 | Helfet |
| 5,219,362 A | 6/1993 | Tuke et al. |
| 5,370,701 A | 12/1994 | Finn |

(Continued)

FOREIGN PATENT DOCUMENTS

| | | |
|---|---|---|
| EP | 1604623 A1 | 12/2005 |
| EP | 2572677 A1 | 3/2013 |

(Continued)

OTHER PUBLICATIONS

Blaha, et al., "Advance Medial-Pivot and Stemmed Medial-Pivot Knee Systems," Wright Medical Technology, Inc. 2010.

(Continued)

*Primary Examiner* — Ann Schillinger
(74) *Attorney, Agent, or Firm* — Barnes & Thornburg LLP

(57) ABSTRACT

An orthopaedic prosthesis system and associated instrumentation is disclosed. The system includes femoral and tibial components configured to be used in a number of different implanted configurations. The instrumentation is configured to facilitate preparation of the bones and selection of the implant configuration. A method of using the system is also disclosed.

10 Claims, 23 Drawing Sheets

(56) References Cited

U.S. PATENT DOCUMENTS

| | | | |
|---|---|---|---|
| 5,405,349 A * | 4/1995 | Burkinshaw | A61B 17/1675 606/88 |
| 5,486,178 A * | 1/1996 | Hodge | A61B 17/155 606/88 |
| 5,662,656 A * | 9/1997 | White | A61B 17/155 606/88 |
| 5,667,512 A * | 9/1997 | Johnson | A61B 17/158 606/88 |
| 5,682,886 A | 11/1997 | Delp et al. | |
| 5,709,689 A * | 1/1998 | Ferrante | A61B 17/1764 606/88 |
| 5,735,856 A * | 4/1998 | McCue | A61B 17/155 606/88 |
| 5,769,854 A * | 6/1998 | Bastian | A61B 17/1604 606/88 |
| 5,810,829 A * | 9/1998 | Elliott | A61B 17/155 606/88 |
| 5,871,018 A | 2/1999 | Delp et al. | |
| 5,964,808 A | 10/1999 | Blaha et al. | |
| 6,013,103 A | 1/2000 | Kaufman et al. | |
| 6,033,410 A * | 3/2000 | McLean | A61B 17/155 606/88 |
| 6,258,095 B1 * | 7/2001 | Lombardo | A61B 17/154 606/88 |
| 6,986,791 B1 | 1/2006 | Metzger | |
| 7,115,133 B2 * | 10/2006 | Plumet | A61B 17/155 606/88 |
| 7,261,740 B2 | 8/2007 | Tuttle et al. | |
| 7,674,268 B2 * | 3/2010 | Cuckler | A61B 17/1764 606/86 R |
| 8,187,335 B2 | 5/2012 | Wyss et al. | |
| 8,192,498 B2 | 6/2012 | Wagner et al. | |
| 8,211,181 B2 | 7/2012 | Walker | |
| 8,236,061 B2 | 8/2012 | Heldreth et al. | |
| 8,292,964 B2 | 10/2012 | Walker | |
| 8,328,873 B2 | 12/2012 | Metzger et al. | |
| 8,480,752 B2 | 7/2013 | Dun | |
| 8,480,762 B2 | 7/2013 | Yoshimitsu | |
| 8,628,579 B2 | 1/2014 | Ries et al. | |
| 8,771,280 B2 * | 7/2014 | Bailey | A61F 2/389 606/88 |
| 8,784,496 B2 | 7/2014 | Wagner et al. | |
| 8,795,380 B2 | 8/2014 | Heldreth et al. | |
| 8,828,086 B2 | 9/2014 | Williams et al. | |
| 8,834,575 B2 | 9/2014 | Wyss et al. | |
| 8,915,965 B2 | 12/2014 | Komistek | |
| 9,050,107 B2 * | 6/2015 | Sordelet | A61B 17/164 |
| 9,101,393 B2 | 8/2015 | Jordan et al. | |
| 9,101,394 B2 | 8/2015 | Arata et al. | |
| 9,168,145 B2 | 10/2015 | Wyss et al. | |
| 9,216,088 B2 | 12/2015 | Wasielewski | |
| 9,220,601 B2 | 12/2015 | Williams et al. | |
| 9,282,981 B2 * | 3/2016 | Chaney | A61B 17/155 |
| 9,299,138 B2 | 3/2016 | Zellner et al. | |
| 9,320,616 B2 | 4/2016 | Samuelson et al. | |
| 9,320,624 B2 | 4/2016 | Shin | |
| 9,326,864 B2 | 5/2016 | Wyss et al. | |
| 9,402,726 B2 | 8/2016 | Linderman et al. | |
| 9,452,053 B2 | 9/2016 | Wagner et al. | |
| 9,539,099 B2 | 1/2017 | Heldreth et al. | |
| 9,603,711 B2 | 3/2017 | Bojarski et al. | |
| 9,668,870 B2 | 6/2017 | Wasielewski | |
| 9,788,954 B2 | 10/2017 | Parisi et al. | |
| 9,820,821 B2 | 11/2017 | Aram et al. | |
| 9,861,446 B2 | 1/2018 | Lang | |
| 9,931,216 B2 | 4/2018 | Williams et al. | |
| 9,937,049 B2 | 4/2018 | Wyss et al. | |
| 9,962,264 B2 | 5/2018 | Komistek | |
| 10,080,633 B2 | 9/2018 | Meerbeek et al. | |
| 10,080,663 B2 | 9/2018 | Wasielewski | |
| 10,159,530 B2 | 12/2018 | Lang | |
| 10,179,051 B2 | 1/2019 | Heldreth et al. | |
| 10,179,052 B2 | 1/2019 | Clary et al. | |
| 10,195,056 B2 | 2/2019 | Wogoman et al. | |
| 10,201,429 B2 | 2/2019 | Enomoto et al. | |
| 10,265,180 B2 | 4/2019 | Wyss et al. | |
| 10,278,827 B2 | 5/2019 | Drury et al. | |
| 10,478,307 B2 | 11/2019 | Wasielewski et al. | |
| 10,543,098 B2 | 1/2020 | Williams et al. | |
| 10,729,551 B2 | 8/2020 | Heldreth et al. | |
| 10,849,760 B2 | 12/2020 | Wyss et al. | |
| 11,141,291 B2 | 10/2021 | Wogoman et al. | |
| 11,229,485 B2 | 1/2022 | Otto et al. | |
| 11,324,598 B2 | 5/2022 | Dai et al. | |
| 11,337,823 B2 | 5/2022 | Williams et al. | |
| 11,364,081 B2 | 6/2022 | Dees, Jr. | |
| 11,369,478 B2 | 6/2022 | Wyss et al. | |
| 11,612,488 B2 | 3/2023 | Wogoman et al. | |
| 2003/0009228 A1 | 1/2003 | Figueroa et al. | |
| 2005/0075638 A1 * | 4/2005 | Collazo | A61B 17/1633 606/80 |
| 2005/0107886 A1 | 5/2005 | Crabtree et al. | |
| 2005/0278035 A1 | 12/2005 | Wyss et al. | |
| 2008/0262812 A1 | 10/2008 | Arata et al. | |
| 2008/0269596 A1 | 10/2008 | Revie et al. | |
| 2009/0088860 A1 | 4/2009 | Romeis et al. | |
| 2009/0125114 A1 * | 5/2009 | May | A61F 2/38 623/20.14 |
| 2009/0204221 A1 | 8/2009 | Walker | |
| 2010/0036499 A1 | 2/2010 | Pinskerova | |
| 2010/0168753 A1 * | 7/2010 | Edwards | A61B 17/1675 606/88 |
| 2010/0286788 A1 | 11/2010 | Komistek | |
| 2012/0197409 A1 | 8/2012 | Mckinnon et al. | |
| 2012/0265496 A1 | 10/2012 | Mahfouz | |
| 2012/0310246 A1 * | 12/2012 | Belcher | A61F 2/4684 606/89 |
| 2012/0310362 A1 | 12/2012 | Li et al. | |
| 2013/0006373 A1 | 1/2013 | Wyss et al. | |
| 2013/0197653 A1 | 8/2013 | Hawkins et al. | |
| 2013/0197654 A1 | 8/2013 | Samuelson et al. | |
| 2013/0325021 A1 * | 12/2013 | Sordelet | A61B 17/155 606/89 |
| 2014/0039635 A1 | 2/2014 | Bartels et al. | |
| 2014/0081412 A1 | 3/2014 | Metzger | |
| 2014/0148811 A1 * | 5/2014 | Reeve | A61B 17/1764 606/88 |
| 2014/0277534 A1 | 9/2014 | Wasielewski | |
| 2014/0330388 A1 | 11/2014 | Mizuguchi et al. | |
| 2015/0032215 A1 | 1/2015 | Slamin et al. | |
| 2015/0088264 A1 | 3/2015 | Li et al. | |
| 2015/0190235 A1 | 7/2015 | Mcminn | |
| 2016/0030184 A1 | 2/2016 | Whiteside | |
| 2016/0262771 A1 * | 9/2016 | Edwards | A61B 17/1615 |
| 2016/0317312 A1 | 11/2016 | Bojarski et al. | |
| 2017/0020674 A1 | 1/2017 | Walker | |
| 2017/0079801 A1 | 3/2017 | Drury et al. | |
| 2017/0128219 A1 | 5/2017 | Metzger et al. | |
| 2017/0189191 A1 | 7/2017 | Heldreth et al. | |
| 2017/0189195 A1 | 7/2017 | Blaha | |
| 2017/0266013 A1 | 9/2017 | Enomoto et al. | |
| 2017/0340389 A1 | 11/2017 | Otto et al. | |
| 2019/0209331 A1 | 7/2019 | Varadarajan et al. | |
| 2019/0209333 A1 | 7/2019 | Drury et al. | |
| 2019/0240032 A1 | 8/2019 | Wasielewski et al. | |
| 2020/0069432 A1 | 3/2020 | Mcminn | |
| 2020/0085583 A1 | 3/2020 | Hodge | |
| 2020/0100902 A1 | 4/2020 | Wasielewski et al. | |
| 2020/0214843 A1 | 7/2020 | Radermacher et al. | |
| 2020/0246149 A1 | 8/2020 | Matyas et al. | |
| 2022/0079678 A1 | 3/2022 | Duxbury et al. | |

FOREIGN PATENT DOCUMENTS

| | | | |
|---|---|---|---|
| EP | 3854353 A1 | 7/2021 | |
| WO | 9723172 A2 | 7/1997 | |
| WO | WO-2005006993 A2 * | 1/2005 | A61B 17/025 |
| WO | 2010151564 A1 | 12/2010 | |
| WO | 2011075697 A2 | 6/2011 | |
| WO | 2014143538 A1 | 9/2014 | |

(56) References Cited

FOREIGN PATENT DOCUMENTS

| WO | 2017155995 A1 | 9/2017 |
| WO | 2017160889 A1 | 9/2017 |
| WO | 2017204832 A1 | 11/2017 |

OTHER PUBLICATIONS

"Persona The Personalized Knee Surgical Technique," Zimmer Biomet, 2018.
"Persona The Personalized Knee, Medial Congruent Bearing Design Rationale," Zimmer Biomet, 2017.
"eMP Evolution Medial-Pivot Knee System, The ACL-PCL Substituting Knee, Key Aspects," MicroPort Orthopedics, Inc., 2015.
"Evolution Medial-Pivot Knee System, Surgical Technique, Distal Cut First Instrumentation," MicroPort Orthopedics, Inc., 2014.
PCT Search Report & Written Opinion prepared for PCT/EP2021/069244, dated Nov. 1, 2022, 24 pages.
Smith & Nephew, Journey II TKA Total Knee System—Combined Technique for Journey II BCS and Journey II CR, 68 pages.
International SR and Written Opinion for International App. No. PCT/US2020/022123, Completed May 8, 2020, 13 Pages.
International SR and Written Opinon for International App. No. PCT/US2020/022119, Completed May 27, 2020, 11 Pages.
International SR for International App. No. PCT/IB20/54105, dated Aug. 31, 2020, 3 Pages.
PCT International SR for International App. No. PCT/IB20/54110, dated Aug. 12, 2020, 3 Pages.
PCT International SR and Written Opinion for International App. No. PCT/EP2020/075246, dated Mar. 15, 2022, 11 Pages.

\* cited by examiner

ORTHOPAEDIC KNEE PROSTHESIS SYSTEM AND METHODS FOR USING SAME

This application claims priority under 35 U.S.C. § 119 to U.S. Provisional Patent Application Ser. No. 62/898,256, which was filed on Sep. 10, 2019 and is hereby incorporated herein by reference.

TECHNICAL FIELD

The present disclosure relates to orthopaedic knee prosthesis systems and, more specifically, to orthopaedic knee prostheses, instrumentation, and methods for total knee arthroplasty procedures.

BACKGROUND

The knee is the largest joint in the body. Normal knee function is required to perform most everyday activities. The knee is made up of the lower or distal end of the femur, which rotates on the upper or proximal end of the tibia, and the patella, which slides in a groove on the end of the femur. Large ligaments attach to the femur and tibia to provide stability as the knee moves between extension and flexion. The long thigh muscles give the knee strength and produces knee motion.

The joint surfaces where these three bones touch are covered with articular cartilage, a smooth substance that cushions the bones and enables them to move easily. The condition of this cartilage on the knee joint is a key aspect of normal knee function and is important to the physician when evaluating a potential need for a knee joint replacement.

All remaining surfaces of the knee are covered by a thin, smooth tissue liner called the synovial membrane. This membrane releases a special fluid that lubricates the knee, reducing friction to nearly zero in a healthy knee.

Normally, all of these components work in harmony. But disease or injury can disrupt this harmony, resulting in pain, muscle weakness, and reduced function.

In addition to the smooth cartilage lining on the joint surfaces, there are two smooth discs of cartilage that cushion the space between the bone ends. The inner disc is called the medial meniscus, while the disc on the outer side of the knee joint is called the lateral meniscus. The role of the menisci is to increase the conformity of the joint between the femur and the tibia. The menisci also play an important function as joint shock absorbers by distributing weight-bearing forces, and in reducing friction between the joint segments.

There are also four major ligaments that play an important part in stability of the knee joint. The Medial Collateral Ligament (MCL) and the Lateral Collateral Ligament (LCL) are located on opposing sides on the outside of the joint. The Anterior Cruciate Ligament (ACL) and the Posterior Cruciate Ligament (PCL) are more centrally located ligaments within the joint. The ACL attaches to the knee end of the femur, at the back of the joint and passes down through the knee joint to the front of the flat upper surface of the tibia. The ACL contacts the femur on the inner lateral condyle. When disrupted, this allows for laxity to occur on the lateral side of the knee. The ACL passes across the knee joint in a diagonal direction, with the PCL passing in the opposite direction, forming a cross shape, hence the name cruciate ligaments. As the knee moves from flexion into full extension, the tibia rotates relative to the femur and the cruciate ligaments tighten to lock the knee and provide greater stability. This rotation of the tibia relative to the femur has been referred to as a "screw-home" mechanism.

Total knee replacement (TKR), also referred to as total knee arthroplasty (TKA), is a surgical procedure where worn, diseased, or damaged surfaces of a knee joint are removed and replaced with artificial surfaces. Materials used for resurfacing of the joint are not only strong and durable but also optimal for joint function as they produce as little friction as possible.

The "artificial joint or prosthesis" generally has three components: (1) a distal femoral component usually made of a biocompatible material such as metal alloys of cobalt-chrome or titanium; (2) a proximal tibial component also made of cobalt chrome or titanium alloy; and (3) a bearing component disposed between the two components, usually formed of a plastic material like polyethylene. In some cases, the proximal tibial component and the bearing component are combined into a single, monolithic component.

In total knee arthroplasty (TKA), there are a number of types of techniques with associated implants. The first main type is the posterior cruciate retaining (CR) total knee arthroplasty, where the surgeon retains the posterior cruciate ligament and sacrifices the anterior cruciate ligament. The second main type is the posterior stabilizing (PS) total knee arthroplasty, where the surgeon sacrifices both the anterior cruciate ligament (ACL) and the posterior cruciate ligament (PCL), and the implant prevents the tibia from shifting into an excessively posterior position relative to the femur during, for example, weight bearing activities. With a PS TKA, posterior stabilization is introduced into the TKA by using a cam/post mechanism. The third main type is the posterior cruciate sacrificing (PCS) TKA where the surgeon sacrifices both the ACL and the PCL but does not use a cam/post mechanism for posterior stabilization. Rather, this TKA type uses constraint in the polyethylene to stabilize the antero-posterior movement.

Any of the above three main types of TKA implant can have a fixed bearing (FB) design or a mobile bearing (MB) design. With the fixed bearing design, the polymer insert is either compression molded directly onto the tibial tray or fixed in the tibial tray using a locking mechanism. In a mobile bearing design, the polymer insert is free to either rotate, translate or both rotate and translate.

Although the ACL is sacrificed during the installation of a total knee arthroplasty system, doing so can have a negative clinical impact for some patients. The role of the ACL is to pull the femur in the anterior direction at terminal (full) extension, near full extension, and in early flexion. The ACL, attached to the lateral condyle of the femur, also works as a tether and keeps the lateral condyle in contact with the lateral meniscus. The PCL pulls the femur in the posterior direction with increasing flexion. The PCL also acts as a tether on the medial condyle of the femur, keeping the medial condyle in contact with the medial meniscus. Together these two ligaments provide the appropriate balance of translational/rotational stability and motion in the knee joint, especially in contact sports and those that involve fast changes in direction and twisting and pivoting movements.

Another type of total knee arthroplasty and associated implants seek to provide anterior stabilization in the absence of a surgically removed ACL and, in some cases, the PCL. One example of an anterior stabilized implant is an implant that is structured to prevent the tibia from shifting into an excessively anterior position relative to the femur during, for example, weight bearing activities. Some examples of this type of TKA, which is sometimes called ACL Substituting TKA (ASTKA), and their associated implants, are shown and described in U.S. Pat. Nos. 10,179,052 and 9,962,264, which are expressly incorporated herein by reference.

SUMMARY

According to one aspect of the disclosure, an orthopaedic prosthetic system is disclosed. The system includes femoral and tibial components configured to be used in a number of different implanted configurations.

According to another aspect, the orthopaedic prosthetic system includes instrumentation configured to facilitate preparation of the bones and selection of the implant configuration.

According to another aspect, a method of using the orthopaedic prosthetic system is also disclosed.

According to another aspect, an orthopaedic prosthesis system may include a femoral component, a tibial tray component and a plurality of tibial insert components. The femoral component may be configured to be coupled to a distal end of a patient's femur and may include a pair of condyles and a notch extending from an open posterior end that is defined between the pair of condyles. The tibial tray component may be configured to be coupled to a proximal end of a patient's tibia. Each of the plurality of tibial insert components may be configured to be separately attached to the tibial tray component and may each include an anterior end, a posterior end, and medial and lateral concave surfaces shaped to engage the condyles of the femoral component.

In some embodiments, the plurality of tibial insert components includes a first tibial insert component and a second tibial insert component. Additionally, an anterior-posterior dimension may be defined between the anterior end and the posterior end of each of the plurality of tibial insert components, and the anterior-posterior dimension of the first tibial insert component may be substantially equal to the anterior-posterior dimension of the second tibial insert component. Additionally, the medial concave surface of the first tibial insert component may have a distal-most point positioned a first distance from the posterior end of the first tibial insert component when the first tibial insert component is viewed in a first sagittal plane. Further, the medial concave surface of the second tibial insert component may have a distal-most point positioned a second distance from the posterior end of the second tibial insert component when the second tibial insert component is viewed in a second sagittal plane, the second distance being greater than the first distance.

In some embodiments, the femoral component may be a first femoral component of a plurality of femoral components and each femoral component may have a different configuration from the other femoral components of the plurality of femoral components. For example, the different configuration of each femoral component may include at least one of size and shape. Additionally, in some embodiments, at least one condyle of the pair of condyles of the femoral component may include an arcuate surface having a curved section that is defined by a continually decreasing radius of curvature when the femoral component is viewed in a third sagittal plane.

In some embodiments, the plurality of femoral components may include a second femoral component including a pair of condyles, a notch extending from an open posterior end that is defined between the pair of condyles, and a cam positioned adjacent an anterior end of the notch. In such embodiments, the plurality of tibial insert components may include a third tibial insert component having a post positioned between the medial and lateral concave surfaces, the medial concave surface of the third tibial insert component may have a distal-most point positioned a third distance from the posterior end of the third tibial insert component when the third tibial insert component is viewed in a third sagittal plane, and the third distance of the third tibial insert component may be less than the second distance of the second tibial insert component. The second femoral component may be configured to rotate relative to the third tibial component between a full extension position and a full flexion position, and the cam and the post are sized, shaped, and positioned so that the cam engages the post when the femoral component is in the full extension position. Additionally, in such embodiments, the anterior-posterior dimension of the third tibial insert component may be substantially equal to the anterior-posterior dimension of the second tibial insert component.

Additionally, in some embodiments, the medial concave surface of each tibial insert component may have an anterior edge. A first height may be defined between the anterior edge and the distal-most point of the medial concave surface of the first tibial insert component when the first tibial insert component is viewed in the first sagittal plane. And, a second height may be defined between the anterior edge and the distal-most point of the medial concave surface of the second tibial insert component when the second tibial insert component is viewed in the second sagittal plane, the second height being less than the first height. Additionally, in some embodiments, the medial concave surface of each tibial insert component may have a posterior edge. A third height may be defined between the posterior edge and the distal-most point of the first tibial insert component when the first tibial insert component is viewed in the first sagittal plane. And, a fourth height may be defined between the posterior edge and the distal-most point of the second tibial insert component when the second tibial insert component is viewed in the second sagittal plane, the fourth height being equal to the third height.

In some embodiments, the medial concave surface of each tibial insert component may have a plurality of radii of curvature. The plurality of radii of curvature of the first tibial insert component may include a first anterior radius of curvature when the first tibial insert component is viewed in the first sagittal plane. And, the plurality of radii of curvature of the second tibial insert component may include a second anterior radius of curvature when the second tibial insert component is viewed in the second sagittal plane. In such embodiments, the second anterior radius of curvature may be greater than the first anterior radius of curvature.

Additionally, in some embodiments, the tibial tray component may include a first portion of a locking mechanism configured to separately secure each of the plurality of tibial insert components to the tibial tray component in place of the other tibial insert components to form a single tibial component. In such embodiments, each tibial insert component may include a second portion of the locking mechanism. Additionally, in some embodiments, the medial concave surface and the lateral concave surface of the first tibial insert component may be asymmetrical, and the medial concave surface and the lateral concave surface of the second tibial insert component may be symmetrical.

According to yet another aspect, a tibial insert component may include a medial concave surface and a lateral concave surface. The medial concave surface may be shaped to engage a medial condyle of a femoral component. The lateral concave surface may be shaped to engage a lateral condyle of the femoral component and wherein the lateral concave surface extends from an anterior edge to a posterior edge. The medial and lateral concave surfaces may be asymmetric relative to each other, and the lateral concave surface may include a distal-most section that defines a straight line when the tibial insert component is viewed in a first sagittal plane.

In some embodiments, the tibial insert component may further include an anterior end and a posterior end. In such embodiments, an anterior-posterior dimension of the tibial insert component may be defined between the anterior end and the posterior end, and the medial concave surface includes a distal-most point that is positioned, relative to the posterior end, a percentage of the anterior-posterior dimension in the range of 33% to 39%.

Additionally, in some embodiments, the medial concave surface includes a distal-most point. A first height may be defined between an anterior edge of the medial concave surface and the distal-most point of the medial concave surface when the tibial insert component is viewed in a second sagittal plane. A second height may be defined between an anterior edge of the lateral concave surface and the distal-most section of the lateral concave surface when the tibial insert component is viewed in the first sagittal plane.

According to another aspect, a method for performing an orthopaedic surgical procedure on a knee joint of a patient may include resecting a tibia and a femur of the knee joint of the patient and attaching a tibial tray component to a resected proximal surface of the tibia of the knee joint of the patient. The tibial tray component may include a first portion of a locking mechanism. The method may also include selecting a tibial insert component from a plurality of tibial insert components. Each tibial insert component of the plurality of tibial insert components may be configured to be separately attached to the tibial tray component and may include a second portion of the locking mechanism to secure the corresponding tibial insert component to the tibial tray component. The plurality of tibial insert components may include a first tibial insert component and a second tibial insert component.

The method may further include attaching the selected tibial insert component to the tibial tray component, which may include coupling the first portion of the locking mechanism to the second portion of the locking mechanism to secure the selected tibial insert component to the tribal base. Each of the first and second tibial insert components may include a medial concave surface shaped to engage a medial condyle of a femoral component and a lateral concave surface shaped to engage a lateral condyle of the femoral component. The medial and lateral concave surfaces of the first tibial insert component may be asymmetrical relative to each other and the medial and lateral concave surfaces of the second tibial insert component may be symmetrical relative to each other.

In some embodiments, selecting the tibial insert component may include selecting either the first tibial insert component or the second tibial insert component. Additionally or alternatively, selecting the tibial insert component from a plurality of tibial insert components may include selecting a tibial insert trial component from a plurality of tibial insert trial components.

Additionally, in some embodiments, each of the first and second tibial insert components includes an anterior end and a posterior end. The medial concave surface of the first tibial insert component may include a distal-most point positioned a first distance from the posterior end of the first tibial insert component when the first tibial insert component is viewed in a first sagittal plane. Additionally, the medial concave surface of the second tibial insert component may include a distal-most point positioned a second distance from the posterior end of the second tibial insert component when the second tibial insert component is viewed in a second sagittal plane, the second distance being greater than the first distance.

In some embodiments, the medial concave surface of each tibial insert component has an anterior edge. A first height may be defined between the anterior edge and the distal-most point of the medial concave surface of the first tibial insert component when the first tibial insert component is viewed in the first sagittal plane. A second height may be defined between the anterior edge and the distal-most point of the medial concave surface of the second tibial insert component when the second tibial insert component is viewed in the second sagittal plane, the second height being less than the first height.

Additionally, in some embodiments, selecting the tibial insert component from the plurality of tibial insert components may include selecting a third tibial insert component from the plurality of tibial insert components. In such embodiments, the third tibial insert component may include a medial concave surface shaped to engage the medial condyle of the femoral component, a lateral concave surface shaped to engage the lateral condyle of the femoral component, and a post positioned between the medial and lateral concave surfaces, wherein the medial and lateral concave surfaces of the third tibial insert are asymmetrical relative to each other.

According to a further aspect, an orthopaedic surgical instrument includes an anterior plate and a distal plate. The anterior plate may be configured to engage an anterior surface of a patient's femur. The distal plate may be attached to, and extend from, the anterior plate to a posterior end. The distal plate may be configured to engage a distal surface of the patient's femur. Additionally, the orthopaedic surgical instrument may further include a notch cutting guide slot defined by a plurality of inner walls. The anterior plate may include a first inner wall of the plurality of inner walls, and the first inner wall may include a distal cutting guide surface configured to guide a resection of a distal portion of an intercondylar notch of the patient's femur to resize the intercondylar notch to receive a cam of a femoral component. The plurality of inner walls may also include a second inner wall having a posterior cutting guide surface configured to guide a resection of a posterior portion of the intercondylar notch of the patient's femur. The posterior cutting guide surface may include a first edge and a second edge and may be sloped such that the first edge is positioned more anterior than the second edge to protect a posterior-cruciate ligament (PCL) of the patient during resection.

The orthopaedic surgical instrument may also include an adjustable body configured to move relative to the anterior plate and the distal plate to change the configuration of the notch cutting guide slot. The adjustable body may include the second inner wall. In some embodiments, the adjustable body may include a third inner wall extending in a direction opposite the second inner wall. The third inner wall may have a posterior cutting guide surface configured to guide a resection of a posterior portion of an intercondylar notch of a patient's other femur. The posterior cutting guide surface may include a first edge and a second edge and may be sloped such that the first edge of the third inner wall is positioned more anterior than the second edge of the third inner wall to protect a posterior-cruciate ligament (PCL) connected to the patient's other femur during resection.

Additionally, in some embodiments, the adjustable body may be operable to slide relative to the anterior plate and the distal plate between a first position in which the second inner wall defines a portion of the notch cutting guide slot and a second position in which the third inner wall defines a portion of the notch cutting guide slot. Additionally, the distal plate may include a first passageway and a second passageway positioned opposite the first passageway. In such embodiments, the third inner wall may be sized to be positioned in the first passageway when the adjustable body is in the first position, and the second inner wall may be sized to be positioned in the second passageway when the adjustable body is in the second position.

In some embodiments, the adjustable body includes a first arm extending anteriorly from the second inner wall and a second arm extending proximally from the first arm. The first arm and the second arm may include a medial cutting guide surface configured to guide a resection of a medial side of the intercondylar notch of the patient's femur.

Additionally, in some embodiments, a central axis of the orthopaedic surgical instrument extends in an anterior-posterior direction through the anterior plate when the orthopaedic surgical instrument is viewed in a transverse plane. In such embodiments, the notch cutting guide slot may have a longitudinal axis that extends parallel to the central axis when the orthopaedic surgical instrument is viewed in a transverse plane, the longitudinal axis being laterally offset from the central axis.

According to another aspect, an orthopaedic surgical instrument may include an anterior plate, a distal plate, an elongated slot defined in the anterior plate and the distal plate, and an adjustable body positioned in the elongated slot. The anterior plate may be configured to engage an anterior surface of a patient's femur. The distal plate may be attached to, and extend from, the anterior plate to a posterior end. The distal plate may be configured to engage a distal surface of the patient's femur. The adjustable body may cooperate with the anterior plate and the distal plate to define a notch cutting guide slot in the orthopaedic surgical instrument. Additionally, the adjustable body may be moveable relative to the anterior plate and the distal plate to change the shape of the notch cutting guide slot. For example, the adjustable body may be movably coupled to the distal plate and operable to slide relative to the anterior plate and the distal plate within the elongated slot.

In some embodiments, the adjustable body may include a first posterior arm and a second posterior arm extending in a direction opposite the first posterior arm. In such embodiments, the adjustable body may be moveable between a first position in which the first posterior arm cooperates with the anterior plate and the distal plate to define a first notch cutting guide slot sized and positioned to resect a patient's left femur, and a second position in which the second posterior arm cooperates with the anterior plate and the distal plate to define a second notch cutting guide slot sized and positioned to resect a patient's right femur.

Additionally, in some embodiments, the first posterior arm may have a first posterior cutting guide surface including a first edge and a second edge. The first posterior cutting guide surface may be sloped such that the first edge of the first posterior arm is positioned more anterior than the second edge to protect a posterior-cruciate ligament (PCL) of the patient's left femur when the adjustable body is positioned in the first position. Similarly, the second posterior arm may have a second posterior cutting guide surface including a third edge and a fourth edge. The second posterior cutting guide surface may be sloped such that the third edge of the second posterior arm is positioned more anterior than the fourth edge to protect a posterior-cruciate ligament (PCL) of the patient's right femur when the adjustable body is positioned in the second position.

According to yet another aspect, a method for performing an orthopaedic surgical procedure on a patient may include resecting a distal end of a femur of the patient to form a planar distal surface on the femur and adjusting an adjustable body of a cutting guide block based on whether the femur is a left femur of the patient or a right femur of the patient. The adjustable body may cooperate with an anterior plate and a distal plate of the cutting guide block to define an intercondylar notch cutting guide slot. The method may also include attaching the cutting guide block to the planar distal surface of the femur and resecting a posterior portion of an intercondylar notch of the femur using the intercondylar notch guiding guide slot of the cutting guide block to resize the intercondylar notch to receive a cam of a femoral component.

In some embodiments, adjusting the adjustable body may include sliding the adjustable body along a rod received in the distal plate. Additionally, sliding the adjustable body may include inserting an inner wall of the adjustable body into a passageway formed in the distal plate.

Additionally, in some embodiments, resecting the posterior portion of the intercondylar notch of the femur may include resecting the posterior portion of the intercondylar notch of the femur using an inner wall of the anterior plate of the cutting guide block as a distal cutting guide surface and an inner wall of the adjustable body as a posterior cutting guide surface. In such embodiments, the posterior cutting guide surface is sloped from a first edge to a second edge such that the first edge is positioned more anterior than the second edge. Additionally or alternatively, resecting the posterior portion of the intercondylar notch of the femur may include viewing a portion of the femur through a view port defined in the anterior plate of the cutting guide block while resecting the femur.

In some embodiments, adjusting the adjustable body of the cutting guide block may include moving the adjustable body to a first position. In such embodiments, the method may also include removing, after resecting the posterior portion of the intercondylar notch of the femur, the cutting guide block from the femur; moving the adjustable body of the cutting guide block to a second position different from the first position; attaching the cutting guide block to the other femur of the left or right femur of the patient; and resecting a posterior portion of an intercondylar notch of the other femur using the intercondylar notch guiding guide slot of the cutting guide block. In such embodiments, moving the adjustable body of the cutting guide block to the second position may include sliding the adjustable body along a rod received in the distal plate from the first position to the second position.

Additionally, in some embodiments, the cutting guide block may include a first cutting guide block. In such embodiments, the method may further include resecting a distal end of the other femur of the left or right femur of the patient to form a planar distal surface on the other femur; adjusting an adjustable body of a second cutting guide block based on whether the other femur is the left or right femur of the patient, wherein the adjustable body cooperates with an anterior plate and a distal plate of the second cutting guide block to define an intercondylar notch cutting guide slot; attaching the second cutting guide block to the planar distal surface of the other femur; and resecting a posterior portion of an intercondylar notch of the other femur using the intercondylar notch guiding guide slot of the second cutting guide block.

In some embodiments, adjusting the adjustable body of the first cutting guide block may include sliding the adjustable body of the first cutting guide block along a rod received in the distal plate of the first cutting guide block to a first position relative to the distal plate of the first cutting guide block. In such embodiments, adjusting the adjustable body of the second cutting guide block may include sliding the adjustable body of the second cutting guide block along a rod received in the distal plate of the second cutting guide block to a second position, wherein the second position is different from the first position relative to the distal plate of the corresponding first and second cutting guide blocks.

According to yet a further aspect, an orthopaedic surgical instrument system may include a tibial tray trial component, a fixation pin, and a tibial insert trial component. The tibial tray trial component may be shaped to be positioned on a proximal end of a patient's tibia. The fixation pin may be coupled to the tibial tray trial component. Additionally, the fixation pin may be configured to engage the proximal end of the patient's tibia and define a pivot axis of the tibial tray trial component relative to the proximal end of the patient's tibia when the fixation pin is engaged in the proximal end of the patient's tibia. The tibial insert trial component may be removably attachable to the tibial tray trial component. The tibial insert trial component may also include medial and lateral concave surfaces shaped to engage a femoral component. The medial concave surface may have a distal-most point that is substantially positioned on the pivot axis defined by the fixation pin when the tibial insert trial component is attached to the tibial tray trial component In some embodiments, the tibial insert trial component may further include a post positioned between the medial and lateral concave surfaces. The post may include an anterior surface configured to be engaged by the femoral component.

Additionally, in some embodiments, the tibial tray trial component may include a tibial base trial component having a central passageway and an evaluation component shaped to be substantially positioned in the central passageway, and the fixation pin is coupled to the evaluation component. In such embodiments, the fixation pin may extend through a through-hole of the evaluation component. For example, the fixation pin may be removable from the through-hole of the evaluation component. Alternatively, in other embodiments, the fixation pin may be attached to, and extends distally from, a distal surface of the evaluation component.

In some embodiments, the tibial base trial component may be configured to pivot relative to the evaluation component about the pivot axis. In such embodiments, the fixation pin may be a first fixation pin coupled at a medial end of the evaluation component, and the orthopaedic surgical instrument system may further include a second fixation pin coupled at a lateral end of the evaluation component to prevent rotation of the evaluation component relative to the proximal end of the patient's tibia.

According to another aspect, a method for performing an orthopaedic surgical procedure on a patient may include positioning a tibial tray trial component on a resected proximal end of the patient's tibia and securing the tibial tray trial component to the patient's tibia using a fixation pin. The fixation pin may define a pivot axis of the tibial tray trial component relative to the proximal end of the patient's tibia when the fixation pin is engaged in the proximal end of the patient's tibia. The method may also include attaching a tibial insert trial component to the tibial tray trial component. The tibial insert trial component and the tibial tray trial component may form a tibial trial construct when attached to each other. Additionally, the tibial insert trial component may include a medial and lateral surfaces shaped to engage a femoral component. The method may also include rotating the tibial trial construct about the pivot axis defined by the fixation pin to locate a rotation position of the tibial trial construct relative to the proximal end of the patient's tibia.

In some embodiments, rotating the tibial trial construct may include rotating the tibial trial construct about the pivot axis to a desired rotation position. In such embodiments, the method may further include securing the tibial trial construct in the desired rotation position using a second fixation pin.

Additionally, in some embodiments, positioning the tibial tray trial component may include positioning a tibial base trial component on the resected proximal end of the patient's tibia. And, the tibial base trial component may include a central passageway. In such embodiments, positioning the tibial tray trial component may also include inserting at least a portion of an evaluation component into the central passageway of the tibial base trial component. Additionally, in such embodiments, securing the tibial tray trial component may include inserting the fixation pin through a through-hole of the evaluation component into the patient's tibia. Alternatively, in some embodiments, the evaluation component may include the fixation pin and, in such embodiment, securing the tibial tray trial component may include inserting the evaluation component into the central passageway of the tibial base trial component to cause the fixation pin of the evaluation component to engage the proximal end of the patient's tibia.

Additionally, in some embodiments, the method may further include coupling a shim to a bottom side of the tibial insert trial component. The shim and the tibial insert trial component may form a tibial bearing trial component when attached to each other. In such embodiments, attaching the tibial insert trial component may include attaching the tibial bearing trial component to the tibial tray trial component.

In some embodiments, the method may further include attaching a handle to an anterior side of the tibial tray trial component. In such embodiments, rotating the tibial trial construct may include rotating the tibial trial construct about the pivot axis using the handle.

Additionally, in some embodiments, the tibial insert trial component may further include a post positioned between the medial and lateral concave surfaces, the post including an anterior surface configured to be engaged by the femoral component.

According to another aspect, a method for performing an orthopaedic surgical procedure on a knee joint of a patient may include resecting a distal end of a femur of the knee joint of the patient to form a planar distal surface on the femur, resecting a proximal end of a tibia of the knee joint of the patient to form a planar proximal surface on the tibia, and adjusting an adjustable body of a notch cutting guide block based on whether the femur is a left femur of the patient or a right femur of the patient. The adjustable body may cooperate with an anterior plate and a distal plate of the notch cutting guide block to define an intercondylar notch cutting guide slot.

The method may also include attaching the notch cutting guide block to the planar distal surface of the femur and resecting a posterior portion of an intercondylar notch of the femur using the intercondylar notch guiding guide slot of the notch cutting guide block to resize the intercondylar notch to receive a cam of a femoral component. The method may further include positioning a tibial tray trial component on the planar proximal surface of the tibia and securing the tibial tray trial component to the planar proximal surface of the tibia using a fixation pin. The fixation pin may define a pivot axis of the tibial tray trial component relative to the planar proximal surface of the tibia when the fixation pin is engaged in the planar proximal surface of the tibia.

The method may also include attaching a tibial insert trial component to the tibial tray trial component. The tibial insert trial component and the tibial tray trial component form a tibial trial construct when attached to each other. The tibial insert trial component may include medial and lateral concave surfaces shaped to engage corresponding condyles of the femoral component and a post positioned between the medial and lateral concave surfaces. The post may include an anterior surface configured to be engaged by the cam of the femoral component. The method may also include rotating the tibial trial construct about the pivot axis defined by the fixation pin to locate a rotation position of the tibial trial construct relative to the proximal end of the patient's tibia.

In some embodiments, the method may also include setting a tibial slope of the tibia of the patient. In such embodiments, setting the tibial slope of the tibia of the patient may include attaching a shim to a tibial surface trial component. The shim may include a proximal surface and a distal surface. The proximal surface may be angled relative to the distal surface to provide an amount of slop to the tibial surface trial component when attached to the shim. The method may further include resecting the tibia to form a slope on the tibia based on an angle defined between the proximal surface and the distal surface of the shim. In some embodiments, the angle defined between the proximal surface and the distal surface of the shim may be in the range of −5 degrees to 10 degrees.

According to yet a further aspect, an orthopaedic surgical instrument system may include a tibial base trial component, an evaluation component, and a tibial insert trial component. The tibial base trial component may be shaped to be positioned on a proximal end of a patient's tibia. The tibial base trial component may also include a first portion of a locking mechanism. The evaluation component may be configured to be coupled to the tibial base trial component and may include a second portion of the locking mechanism. The tibial insert trial component may be configured to be attached to the tibial base trial component to prevent relative rotation of the tibial insert trial component and the tibial base trial component. The first portion of the locking mechanism may be movable from a locked position in which the tibial insert trial component and the tibial base trial component are prevented from rotating relative to the evaluation component to an unlocked position in which the tibial insert trial component and the tibial base trial component are rotatable relative to the evaluation component.

In some embodiments, the first portion of the locking mechanism may include a first plurality of teeth and the second portion of the locking mechanism may include a second plurality of teeth. The first plurality of teeth may be interdigitated with the second plurality of teeth when the first portion of the locking mechanism is in the locked position to prevent rotation of the tibial insert trial component and the tibial base trial component relative to the evaluation component. Additionally, in some embodiments, the first plurality of teeth are disengaged with the second plurality of teeth when the first portion of the locking mechanism is in the unlocked position to permit rotation of the tibial insert trial component and the tibial base trial component relative to the evaluation component. In some embodiments, the first portion of the locking mechanism may be movable to one of a plurality of different locked positions. In such embodiments, when in each locked position, the first plurality of teeth are interdigitated with the second plurality of teeth to prevent rotation of the tibial insert trial component and the tibial base trial component relative to the evaluation component.

Additionally, in some embodiments, the tibial base trial component may be movable in an inferior-superior direction relative to the proximal end of the patient's tibia to move the first portion of the locking mechanism between the locked and unlocked position.

In some embodiments, the first portion of the locking mechanism may include a first plurality of teeth and the second portion of the locking mechanism may include a second plurality of teeth. In such embodiments, the tibial base trial component may be movable from an inferior position at which the tibial base trial component is positioned on the proximal end of the patient's tibia and the first plurality of teeth are interdigitated with the second plurality of teeth to a superior position at which the tibial base trial component is positioned above the proximal end of the patient's tibia and the first plurality of teeth are disengaged with the second plurality of teeth. Additionally, in such embodiments, the tibial base trial component, while positioned in the superior position, may be rotatable to a rotated position relative to the proximal end of the patient's tibia and may be further movable back to the inferior position to re-interdigitate the first plurality of teeth with the second plurality of teeth to prevent rotation of the tibial insert trial component and the tibial base trial component relative to the evaluation component when in the rotated position relative to the proximal end of the patient's tibia.

Additionally, in some embodiments, the first portion of the locking mechanism may include a first plurality of teeth and the second portion of the locking mechanism includes a second plurality of teeth. In such embodiments, the first portion of the locking mechanism may be movable (i) from a first locked position in which a first portion of the first plurality of teeth are interdigitated with the second plurality of teeth to prevent rotation of the tibial insert trial component and the tibial base trial component relative to the evaluation component, (ii) to the unlocked position in which the first plurality of teeth are disengaged with the second plurality of teeth to permit rotation of the tibial insert trial component and the tibial base trial component relative to the evaluation component, and (iii) to a second locked position in which a second portion of the first plurality of teeth are interdigitated with the second plurality of teeth to prevent rotation of the tibial insert trial component and the tibial base trial component relative to the evaluation component. The first locked position may be different from the second locked position. In some embodiments, for example, the unlocked position may be a position that is superior of the first and second locked positions, relative to the proximal end of a patient's tibia.

In some embodiments, the tibial base trial component may include a central passageway shaped to receive a portion of the evaluation component, an inferior surface configured to be positioned on the proximal end of a patient's tibia, a superior surface positioned opposite the inferior surface, and a rim surface positioned between the superior surface and the inferior surface within the central passageway. In such embodiments, the evaluation component may include a medial arm that extends to the medial end. The medial arm may include a flange surface that is configured to engage the rim surface of the tibial base trial component to limit movement of the tibial base trial component in the inferior-superior direction.

Additionally, in some embodiments, the evaluation component may include a central platform, a medial prong that extends outwardly from the central platform, and a lateral prong that extends outwardly from the central platform. In such embodiments, each of the medial and lateral prongs may include a spike configured to engage the proximal end of the patient's tibia when the evaluation component is coupled to the tibial base trial component to prevent rotation of the evaluation component relative to the proximal end of the patient's tibia. Additionally, in such embodiments, the lateral prong may include a lateral tip having a plurality of teeth that define the first portion of the locking mechanism. Additionally or alternatively, the evaluation component may further include a post extending superiorly. In such embodiments, the tibial insert trial component may include a slot shaped to receive the post of the evaluation component when the tibial insert trial component is attached to the tibial base trial component.

According to another aspect, a method for performing an orthopaedic surgical procedure on a patient may include positioning a tibial base trial component on a resected proximal end of a tibia of the patient and coupling an evaluation component to the tibial base trial component. The tibial base trial component may include a first portion of a locking mechanism, and the evaluation component may include a second portion of the locking mechanism. The method may also include attaching a tibial insert trial component to the tibial base trial component to prevent relative rotation of the tibial insert trial component and the tibial base trial component. The method may further include moving the tibial base trial component from an initial position on the resected proximal end of the tibia to a rotated position by moving the first portion of the locking mechanism from a locked position in which the tibial insert trial component and the tibial base trial component are prevented from rotating relative to the evaluation component to an unlocked position in which the tibial insert trial component and the tibial base trial component are rotatable relative to the evaluation component.

In some embodiments, the first portion of the locking mechanism may include a first plurality of teeth and the second portion of the locking mechanism may include a second plurality of teeth. In such embodiments, moving the first portion of the locking mechanism from the locked position to the unlocked position may include moving the first portion of the locking mechanism from the locked position in which the first plurality of teeth are interdigitated with the second plurality of teeth to prevent rotation of the tibial insert trial component and the tibial base trial component relative to the evaluation component to an unlocked position in which the first plurality of teeth are disengaged with the second plurality of teeth to permit rotation of the tibial insert trial component and the tibial base trial component relative to the evaluation component. In such embodiments, the method may further include moving the first portion of the locking mechanism to one of a plurality of different locked position and, in each locked position of the plurality of locked positions, the first plurality of teeth may be interdigitated with the second plurality of teeth to prevent rotation of the tibial insert trial component and the tibial base trial component relative to the evaluation component.

In some embodiments, moving the tibial base trial component from the initial position to a rotated position may include moving the tibial base trial component in an inferior-superior direction relative to the resected proximal end of the tibia to move the first portion of the locking mechanism between the locked and unlocked position.

Additionally, in some embodiments, the first portion of the locking mechanism may include a first plurality of teeth and the second portion of the locking mechanism includes a second plurality of teeth. In such embodiments, moving the tibial base trial component from the initial position to a rotated position may include moving the tibial base trial component from an inferior position at which the tibial base trial component is positioned on the resected proximal end of the tibia and the first plurality of teeth are interdigitated with the second plurality of teeth to a superior position at which the tibial base trial component is positioned above the resected proximal end of the tibia and the first plurality of teeth are disengaged with the second plurality of teeth. Additionally, in such embodiments, moving the tibial base trial component from the initial position to a rotated position may further include rotating the tibial base trial component while the tibial base trial component is positioned in the superior position.

In some embodiments, the first portion of the locking mechanism may include a first plurality of teeth and the second portion of the locking mechanism may include a second plurality of teeth. In such embodiments, moving the tibial base trial component from the initial position to a rotated position may include moving the tibial base trial component from (i) a first inferior position at which the tibial base trial component is positioned on the resected proximal end of the tibia and the first plurality of teeth are interdigitated with the second plurality of teeth to prevent rotation of the tibial insert trial component relative to the evaluation component to (ii) to a superior position at which the tibial base trial component is positioned above the resected proximal end of the tibia and the first plurality of teeth are disengaged with the second plurality of teeth to permit rotation of the tibial insert trial component relative to the evaluation component, rotating the tibial base trial component relative to the evaluation component while the tibial base trial component is in the superior position, and moving the tibial base trial component from the superior position to a second inferior position at which the tibial base trial component is positioned on the resected proximal end of the tibia and the first plurality of teeth are interdigitated with the second plurality of teeth to prevent rotation of the tibial insert trial component relative to the evaluation component while in the second inferior position, wherein the second inferior position is different from the first inferior position.

BRIEF DESCRIPTION OF THE DRAWINGS

The detailed description particularly refers to the following figures, in which.

DETAILED DESCRIPTION OF THE DRAWINGS

Figure 1:
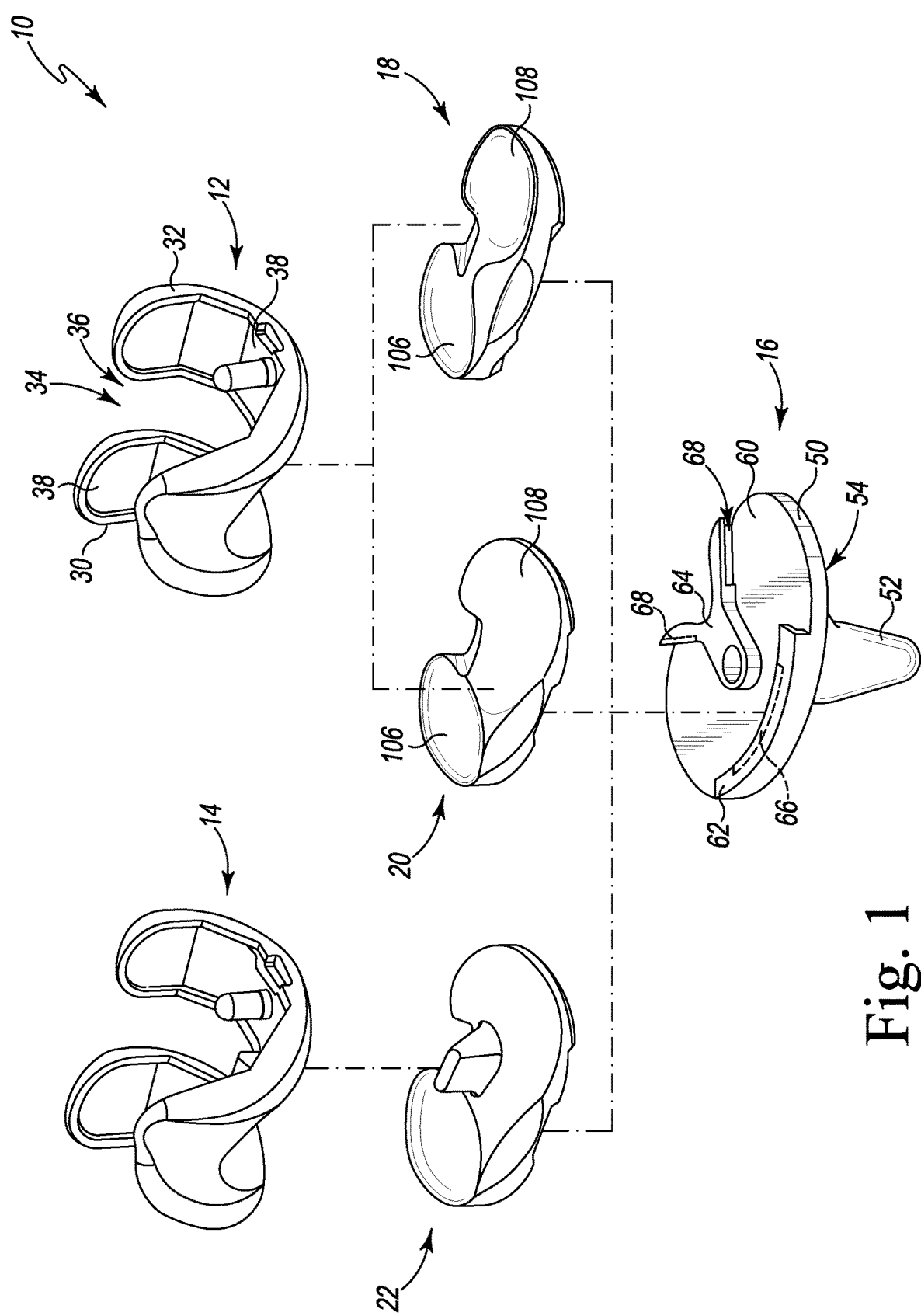
FIG. 1 is an exploded perspective view of an orthopaedic prosthesis system.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

The exemplary embodiments of the present disclosure are described and illustrated below to encompass prosthetic knee joints and knee joint components, as well as methods of implanting and reconstructing knee joints. It will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referring now to FIG. 1, an orthopaedic prosthesis system 10 includes a plurality of femoral components 12, 14, a tibial tray component 16, and a plurality of tibial tray insert components 18, 20, 22 for use in total knee arthroplasty procedures. Each tibial tray insert 18 is configured to be separately attached to the tibial tray 16, which is adapted to be secured to the proximal end of a tibia. When one of the tray inserts is attached to the tibial tray 16, the insert and tray combine to form a single tibial component. In the illustrative embodiment, the tibial tray inserts 18, 20 are configured to engage the femoral component 12 and permit the femoral component 12 to articulate over a range of flexion, while the tibial tray insert 22 is configured to engage the other femoral component 14 to permit the articulation of that component over a range of flexion. In some embodiments, the tibial tray inserts 18, 20 may be configured to also engage with the femoral component 14 and permit the femoral component 14 to articulate over a range of flexion.

As described in greater detail below, the tibial tray insert 18 is a symmetrical posterior cruciate retaining (CR) insert, while the tibial tray insert 20 is an asymmetrical posterior cruciate retaining (CR) insert. The femoral component 14 and the tibial tray insert 22 are ACL-Substituting (AS) components. The asymmetrical CR tray insert 20 and the AS tray insert 22 are configured to cooperate with the femoral components 12, 14, respectively, to provide additional anterior stability on the medial side of the patient's knee relative to the symmetrical CR tray insert 18. In offering a variety of potential cruciate retaining options, the system 10 is configured to provide the surgeon with a number of different implant choices, thereby offering the surgeon flexibility in selecting the appropriate implant configuration to suit the needs of a particular patient. It is also understood that CR designs and the AS design can also be used without the posterior cruciate if the insert is designed with adequate stability to control anterior motion of the femoral component with respect to the insert. It should be appreciated that the system may include additional femoral components and additional tibial tray inserts, such as, for example, a posterior-stabilized femoral component and a posterior-stabilized tray insert, to further extend range of options. In such embodiments, the additional tibial tray inserts may be configured to engage the tibial tray 16.

The femoral components 12, 14 and the tibial tray 16 are illustratively formed from a metallic material such as cobalt-chromium or titanium but may be formed from other materials, such as a ceramic material, a polymer material, a bio-engineered material, or the like, in other embodiments. The tibial tray inserts 18, 20, 22 are illustratively formed from a polymer material such as an ultra-high molecular weight polyethylene (UHMWPE), but may be formed from other materials, such as a ceramic material, a metallic material, a bio-engineered material, or the like, in other embodiments. It should be appreciated that only a single size of each of these components—the femoral components, tray, tray inserts—is shown and described below, the system 10 may include additional sizes of each of those components to accommodate the bony anatomies of various patients.

As shown in FIG. 1, the femoral component 12 is illustratively a posterior cruciate retaining (CR) orthopedic femoral component that includes medial and lateral condyles 30, 32 and a notch 34 between the condyles 30, 32. Each condyle 30, 32 includes an arcuate surface that extends from the posterior end of the condyle 30, 32 to the anterior flange of the femoral component 12. In some embodiments, the arcuate surface may include a curved section that is defined by a gradually or continuously decreasing radius of curvature when the femoral component is viewed in a sagittal plane. For example, the arcuate surface of the femoral component 12 may include an anterior curved section located anteriorly of the curved section having the gradually decreasing radius of curvature and a posterior curved section located posteriorly of the curved section having the gradually decreasing radius of curvature. In such embodiments, the curved section having the gradually decreasing radius of curvature is designed to gradually transition the arcuate surface of the condyle 30, 32 from the radius of curvature of the anterior curved section to the radius of curvature of the posterior curved section. In this way, the anterior curved section, the of curved section having the gradually decreasing radius of curvature, and the posterior curved section (and possibly additional curved sections) form the arcuate surface of the corresponding condyle 30, 32.

The notch 34 of the illustrative femoral component 12 extends from a posterior gap or open end 36 to allow the femoral component 12 to rotate between full extension and full flexion without impinging the posterior cruciate ligament (PCL), which is retained during the total arthroplasty procedure. The femoral component 12 also includes a number of bone-facing surfaces 38 that are configured to confront a surgically-prepared distal end 40 of a patient's femur 42 (see FIG. 17). As described above, the femoral component 12 is configured to engage with (and articulate on) either the tibial tray insert component 18 or the tibial tray insert component 20, which are described in greater detail below.

The tibial tray 16 includes a plate or platform 50 and an elongated stem 52 that extends away from the distal surface 54 of the platform 50. The elongated tibial stem 52 and the platform 50 are configured to be implanted on and into a surgically-prepared proximal end 56 of a patient's tibia 58 (see FIG. 17). The tibial tray 16 also includes a proximal surface 60 that is positioned opposite the distal surface 54 of the platform 50. An anterior buttress 62 and a posterior buttress 64 extend outwardly from the proximal surface 60. Each of the buttresses 62, 64 includes one or more undercuts or channels 66, 68 configured to receive corresponding flanges 70, 72 (see FIG. 2), respectively, of each of the tibial tray inserts 18, 20, 22 to secure one of the inserts to the tray. In that way, the flanges 70, 72 and buttresses 62, 64 cooperate to form a locking mechanism configured to separately secure each insert to the tibial tray in place of the other inserts to form a single tibial component. It should be appreciated that in other embodiments the locking mechanism may take other forms, including, for example, dove-tail joints, fasteners such as screws or pins, or other mechanical interfaces to attach the insert to the tibial tray. It should also be appreciated that the tray may be asymmetrical, with the buttresses shifted medially or laterally on the platform to accommodate different configurations of inserts.

Figure 2:
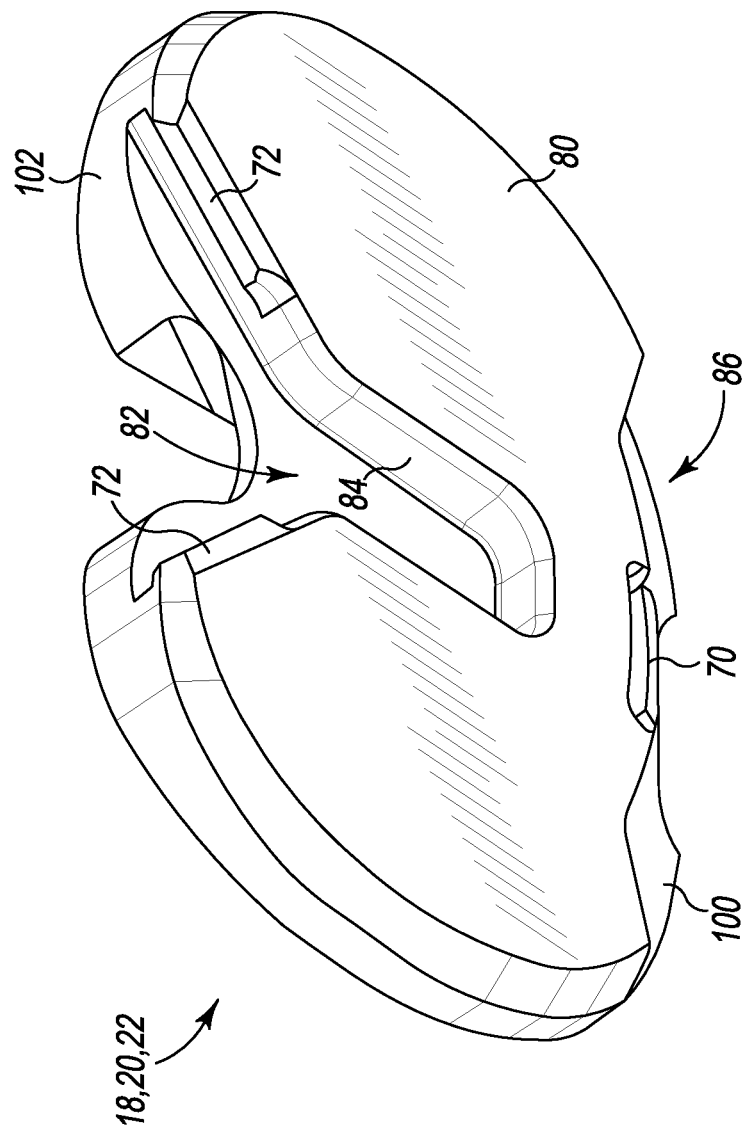
FIG. 2 is a perspective view of a tibial tray insert component of the system of FIG. 1.

Referring now to FIG. 2, each of the tibial tray inserts 18, 20, 22 includes a body 80 that is configured to confront the tibial platform 50. Each insert includes a posterior channel 82 sized and shaped to receive the posterior buttress 64 of the tibial tray 16. The flanges 72 extend inwardly from the sidewalls 84 that define the posterior groove 82 and are positioned to be received in the undercuts 68 of the tibial tray 16. Each insert 18, 20, 22 also includes an anterior channel 86 that is sized and shaped to receive the anterior buttress 62 of the tibial tray 16. The flange 70 is positioned in the anterior channel 86 where it can be received in the undercut 66 of the tibial tray 16 when the insert 18, 20, 22 is assembled with the tibial tray 16. In the illustrative embodiment, the buttresses 62, 64, the flanges 70, 72, and the channels 82, 86 cooperate to lock each tibial tray insert 18, 20, 22 in a single orientation relative to the tibial tray 16. It should be appreciated that in other embodiments the tray and inserts may include mobile bearing interface that allows the tibial tray inserts to move independent of the tibial tray.

Figure 3:
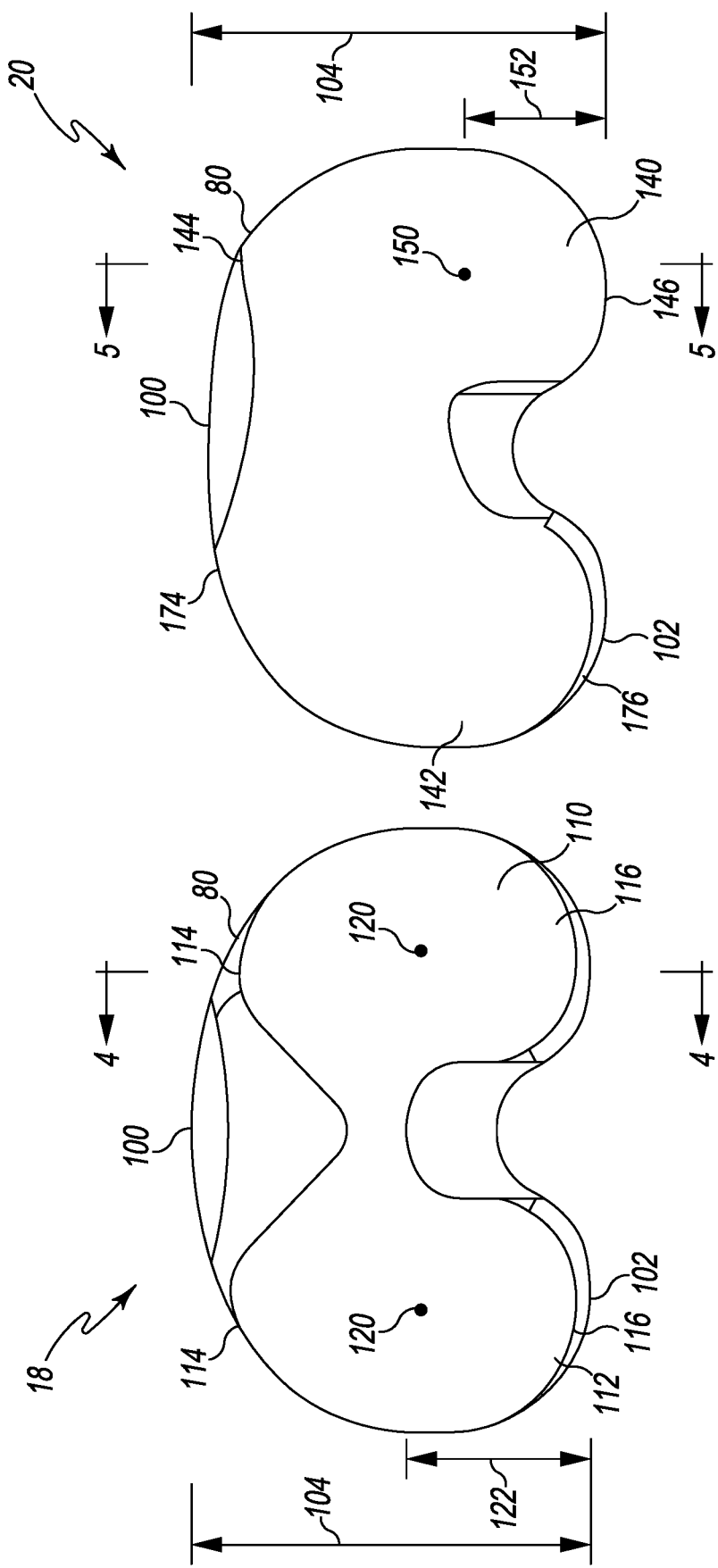
FIG. 3 is a plan view of cruciate retaining tibial tray inserts of the system of FIG. 1.

Referring now to FIG. 3, the body 80 of each of the tibial tray inserts 18, 20 extends from an anterior end 100 to a posterior end 102. This length defines an anterior-posterior distance 104 of each insert 18, 20. As described above, the illustrative embodiment of the system 10 includes only system components that have the same size, and, as shown in FIG. 3, the anterior-posterior distance 104 of the tibial tray insert 18 is substantially equal to the tibial tray insert 20 such that they each may be positioned on the same tibial tray 16. As used in this application, the term "substantially" and derivatives thereof, and words of similar import, when used to describe a size, shape, orientation, distance, spatial relationship, or other parameter includes the stated size, shape, orientation, distance, spatial relationship, or other parameter and also includes a range up to 10% more and up to 10% less than the stated parameter, including 5% more and 5% less, including 3% more and 3% less, including 1% more and 1% less. For example, in some embodiments, the anterior-posterior distance of insert 18 may vary from the anterior-posterior distance of the insert 20 (and insert 22) by 1 to 2 millimeters and may still be considered substantially equal to the anterior-posterior distance of the insert 20 (or the insert 22). In the illustrative embodiment, the anterior-posterior distance 104 of each insert is in a range of 45 to 48 millimeters.

Figure 4:
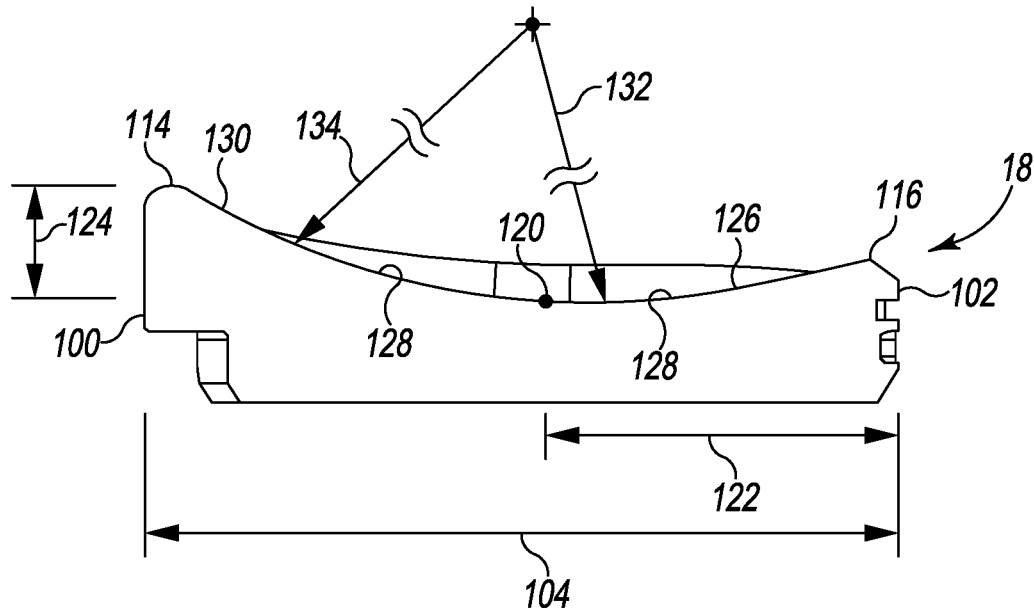
FIG. 4 is a cross-sectional view showing one of the cruciate retaining tibial tray inserts in a sagittal plane along the line 4-4 in FIG. 3.

Each body 80 also includes medial and lateral concave surfaces 106, 108 that are adapted to receive and engage the condyles 30, 32 of the femoral component 12. Turning to the symmetrical CR tray insert 18, the medial and lateral concave surfaces (hereinafter surfaces 110, 112) are symmetrical and, in the illustrative embodiment, are substantially identical. Each surface extends from an anterior edge 114 to a posterior edge 116 within the ends 100, 102 of the insert body 80. As shown in FIGS. 3 and 4, each surface has a distal-most point 120 positioned between the edges 114, 116. An anterior-posterior distance 122 is defined between the distal-most point 120 and the posterior end 102 of the insert 18. In the illustrative embodiment, the anterior-posterior distance 122 is equal to about 21.5 millimeters. The term "about" as used in this application should be understood as referring to dimensions within typical manufacturing tolerances of the materials involved. It should be appreciated that this distance may vary by size of the insert. The position of the distal-most point 120 as a percentage of the total length of insert 18 (i.e., the percentage ratio between the anterior-posterior distance 122 and the anterior-posterior distance 104) is in a range of 44% to 48% in the illustrative embodiment.

In some embodiments, the percentage ratio may be based on an anterior-posterior distance measured from the anterior edge of the tibial tray when the insert 18 is mounted on the tray. In such embodiments, the percentage ratio between that anterior-posterior distance and the anterior-posterior distance 104 may be in a range of 58% to 60%. In some embodiments, that percentage ratio may be equal to about 59%.

As shown in FIG. 4, each of the surfaces 110, 112 has an anterior height 124 that is defined between the distal-most point 120 and the anterior edge 114 of each surface when viewed in a sagittal plane. In the illustrative embodiment, the anterior height 124 is equal to about 6.2 millimeters. In other embodiments, the height may be in a range of 5-7 millimeters. It should be appreciated that this height may vary by size of the insert.

In the illustrative embodiment, the medial and lateral surfaces 110, 112 each define an arc 126 that extends between the anterior edge 114 and the posterior edge 116 when the surfaces are each viewed in the sagittal plane. The arc 126 includes a plurality of arc sections 128, including an anterior arc section 130 extending from the anterior edge 114. Each arc section 128 has a radius of curvature 132. In the illustrative embodiment, the radius of curvature of the anterior arc section 130 is a radius of curvature 134.

Figure 5:
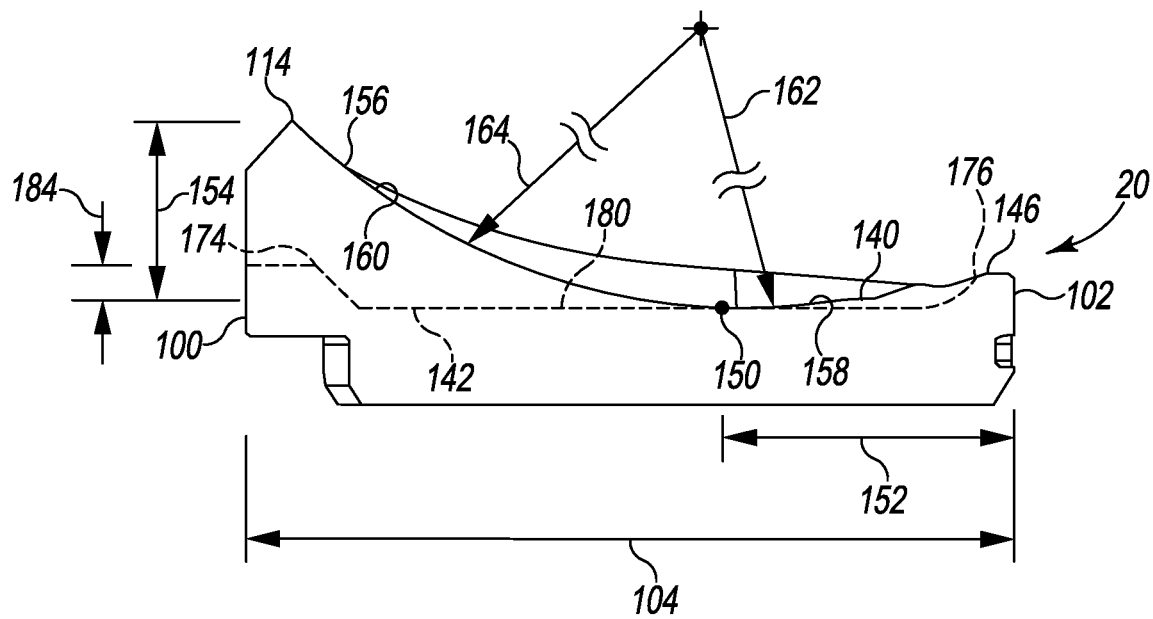
FIG. 5 is a cross-sectional view showing one of the cruciate retaining tibial tray inserts in a sagittal plane along the line 5-5 in FIG. 3.

Turning to the asymmetrical CR tray insert 20 shown in FIGS. 3 and 5, the medial and lateral concave surfaces (hereinafter surfaces 140, 142) are asymmetrical with the lateral concave surface 142 generally flatter than the medial concave surface 140. The medial surface 140 extends from an anterior edge 144 to a posterior edge 146 within the ends 100, 102 of the insert 20. As shown in FIGS. 3 and 5, the medial surface 140 has a distal-most point 150 positioned between the edges 144, 146. An anterior-posterior distance 152 is defined between the distal-most point 150 and the posterior end 102 of the insert 18. In the illustrative embodiment, the anterior-posterior distance 152 is equal to about 17.6 millimeters. In that way, the anterior-posterior distance 152 of the medial surface 140 of the tibial tray insert 20 is less than the corresponding anterior-posterior distance 122 of either of the surfaces 110, 112 of the tibial tray insert 18 such that the distal-most point 150 of the medial surface 140 is more posterior than the distal-most point 120 of each of the surfaces 110, 112. In the illustrative embodiment, the position of the distal-most point 150 of the medial surface 140 as a percentage of the total length of insert 20 (i.e., the percentage ratio between the anterior-posterior distance 152 and the anterior-posterior distance 104) is in a range of 36% to 39% in the illustrative embodiment.

In some embodiments, the percentage ratio may be based on an anterior-posterior distance measured from the anterior edge of the tibial tray 16 when the insert 20 is mounted on the tray 16. In such embodiments, the percentage ratio between that anterior-posterior distance and the anterior-posterior distance 104 may be in a range of 60% to 70%. In some embodiments, that percentage ratio may be equal to about 66%.

As shown in FIG. 5, the medial surface 140 of the insert 20 has an anterior height 154 that is defined between the distal-most point 150 and the anterior edge 144 of the medial surface 140 when viewed in a sagittal plane. In the illustrative embodiment, the anterior height 154 is in a range of 10.6 to 10.7 millimeters. In that way, the anterior height 154 of the medial surface 140 of the insert 20 is greater than the anterior height 124 of either the medial or lateral surfaces 110, 112 of the symmetrical CR tray insert 18.

In the illustrative embodiment, the medial surface 140 defines an arc 156 that extends between the anterior edge 144 and the posterior edge 146 when it is viewed in the sagittal plane. The arc 156 includes a plurality of arc sections 158, including an anterior arc section 160 extending from the anterior edge 144. Each arc section 158 has a radius of curvature 162. In the illustrative embodiment, the radius of curvature of the anterior arc section 160 (hereinafter radius 164) is smaller than the radius of curvature of the corresponding anterior arc section 130 of the symmetrical CR tray insert 18.

As described above, the lateral surface 142 of asymmetrical CR tray insert 20 is generally flatter than the medial surface 140. In the illustrative embodiment, it is also flatter than either of the surfaces 110, 112 of the symmetrical CR tray insert 18. The lateral surface 142 extends from an anterior edge 174 to a posterior edge 176 within the ends 100, 102 of the insert 20. As shown in FIG. 5, the lateral surface 142 has a distal-most section 180 that defines a substantially straight line between the edges 174, 176 and also has an anterior height 184 that is defined between the distal-most section 180 and the anterior edge 174 of the lateral surface when the insert 20 is viewed in a sagittal plane. In the illustrative embodiment, the anterior height 184 is in a range of 2.0 to 2.2 millimeters.

The configuration of the medial concave surface 140 of the asymmetrical CR tray insert 20 provides additional conformity with the medial condyle of the femoral component 12 at extension. That additional conformity, combined with the asymmetry between the concave surfaces 140, 142, assists in providing anterior stabilization of the knee at extension in the absence of the ACL, as well as facilitating the "screw-home" mechanism described above. In the illustrative embodiment, capability of the symmetrical CR tray insert 18 to also interface with the tibial tray 16 provides the surgeon with the option of using either of the CR tray inserts 18, 20 with the femoral component 12, allowing the surgeon to have greater options in selecting the implant configuration appropriate to the patient's needs.

Figure 6:
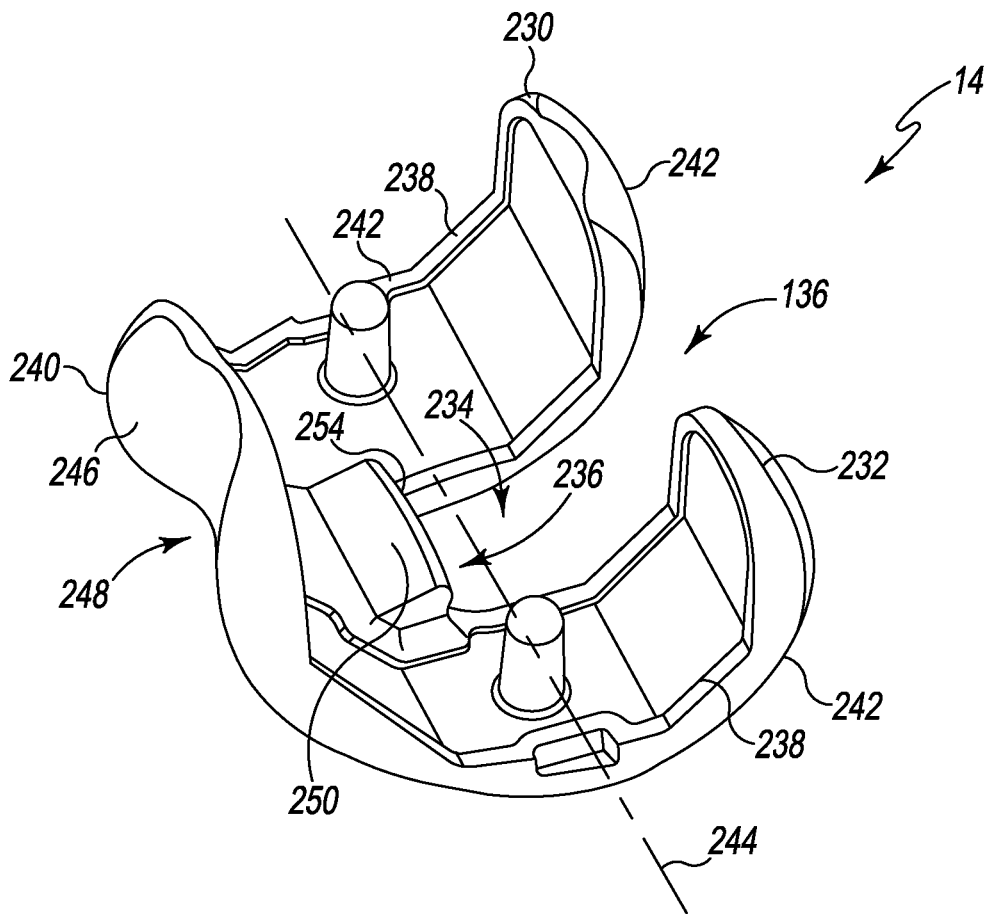
FIG. 6 is an exploded perspective view of an ACL-substituting knee prosthesis.
Figure 6:
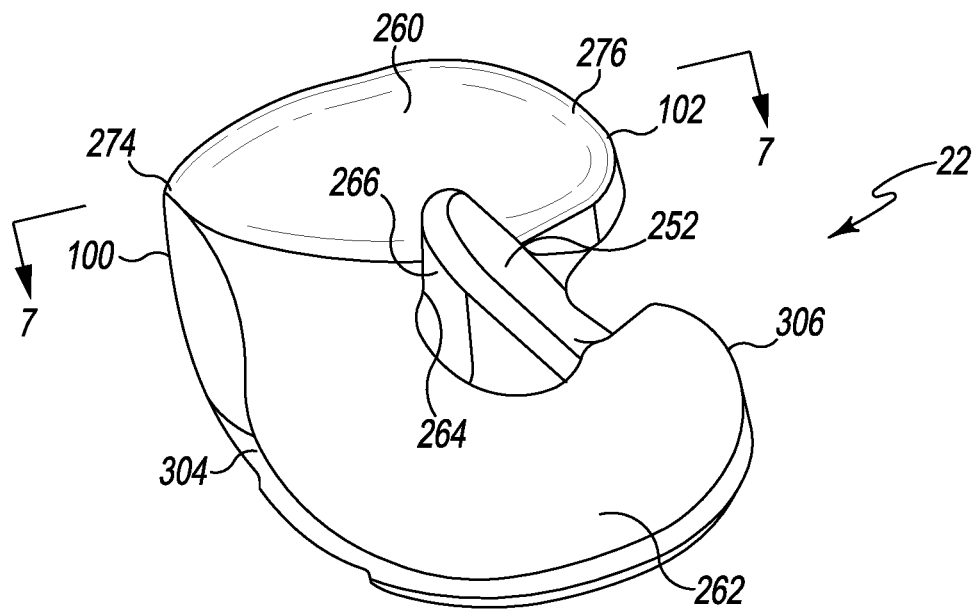

Referring now to FIG. 6, the system 10 also includes a femoral component 14 and a tibial tray insert 22 configured to be separately secured to the tibial tray 16 in place of the other inserts 18, 20. The femoral component 14, like the femoral component 12, has medial and lateral condyles 230, 232 and a notch 234 between the condyles 230, 232. The notch 234 extends from a posterior gap or open end 236 to allow the femoral component 14 to rotate between full extension and full flexion without impinging the PCL. The femoral component 14 includes a number of bone-facing surfaces 238 that are configured to confront the surgically-prepared distal end 40 of the patient femur 42 (see FIG. 17).

The femoral component 14 includes an anterior portion 240 and a posterior portion 242 that are shown by the dotted line imaginary boundary line 244 in FIG. 6. The anterior portion 240 includes a front exterior face 246 having a depression 248 adapted to receive at least a portion of a patella component. The depression 248 marks the beginning of individual condyle 230, 232 formation. From the top or superior-most portion of the front exterior face 246 downward, following the contours of the front face, the curved nature begins to take shape and transition into individual condyles 230, 232. As the shape of the condyles 230, 232 becomes more pronounced, the condyles separate from one another to open the notch 234. Additionally, as illustrated in FIG. 6, the medial condyle 230 has a maximum medial-lateral width that is larger than the maximum medial-lateral width of the lateral condyle 232. However, in the illustrative embodiment, the notch 234 has a substantially uniform width, resulting in the inner shape and contour of the condyles being substantially the same.

The femoral component 14 also has an anterior cam 250 that is positioned at the anterior end of the notch 234 and is configured to engage a spine 252 of the tibial tray insert 22. As described above, the femoral component 14 and tibial tray insert 22 are ACL-Substituting (AS) components configured to provide anterior stabilization and additional support at extension. As shown in FIG. 6, the anterior cam 250 of the femoral component 14 has a posterior surface 254 that is arcuate or rounded. When viewed in the sagittal plane, the posterior surface 254 defines a convex curved line. It should be appreciated that in other embodiments the posterior surface may define a concave curved line. In still other embodiments, the posterior surface may define a substantially straight line for a substantially flat or planar cam. The posterior-most point of the surface 254 is positioned anterior of the boundary line 244, illustrating that the anterior cam 250 is positioned entirely in the anterior portion 240 of the femoral component 14.

As described above, the insert 22 is configured to engage the femoral component 14 and permit the femoral component 14 to articulate over a range of flexion. The tibial tray insert 22 includes medial and lateral concave bearing surfaces 260, 262 that are adapted to receive and engage the condyles 230, 232 of the femoral component 14. The two bearing surfaces 260, 262 are partially separated from one another by a post or spine 252 upstanding from the tibial tray insert 22. In this exemplary embodiment, the spine 252 is integrally formed with the tibial tray insert 22. However, it should be appreciated that the spine 252 may be separable from the tibial tray insert 22 and its location modified based on the location/movement of the tibial tray insert.

The spine 252 has an anterior surface or wall 264 that is configured to engage the posterior surface 254 of the cam 250 of the femoral component 14 at full extension through early flexion. As shown in FIG. 6, the spine 252 also includes a curved anterior section 266 that is sized to ensure the cam 250 properly disengages from the spine 252. It should be appreciated that the spine 252 may include other structures that are sized and shaped to ensure the cam 250 properly disengages from the spine 252 by mid-to-late flexion. In the illustrative embodiment, the anterior section 266 faces toward the medial concave surface 260 and faces away from the lateral concave surface 262.

In the illustrative embodiment, the configuration of the concave surfaces 260, 262 substantially matches the configuration of the corresponding concave surfaces 140, 142 of the insert 20. In other embodiments, the surfaces 260, 262 may continue to be asymmetrical but may share a common posterior geometry before diverging as they progress anteriorly, with the lateral surface 262 having a flatter anterior section than the medial surface 260. In such embodiments, the medial surface 260 may have a distal-most point that is proximate to where the geometries of the surfaces 260, 262 begin to diverge. It should be appreciated that in other embodiments the surfaces 260, 262 may be symmetrical and have substantially identical geometries.

As shown in FIG. 6, the AS insert 22 includes a body 80 that extends from an anterior end 100 to a posterior end 102. This length defines an anterior-posterior distance 104 of the insert. In the illustrative embodiment, the anterior-posterior distance 104 of the tibial tray insert 22 is substantially equal to the tibial tray insert 18, 20 such that they each may be positioned on the same tibial tray 16 in place of the other tray inserts.

Figure 7:
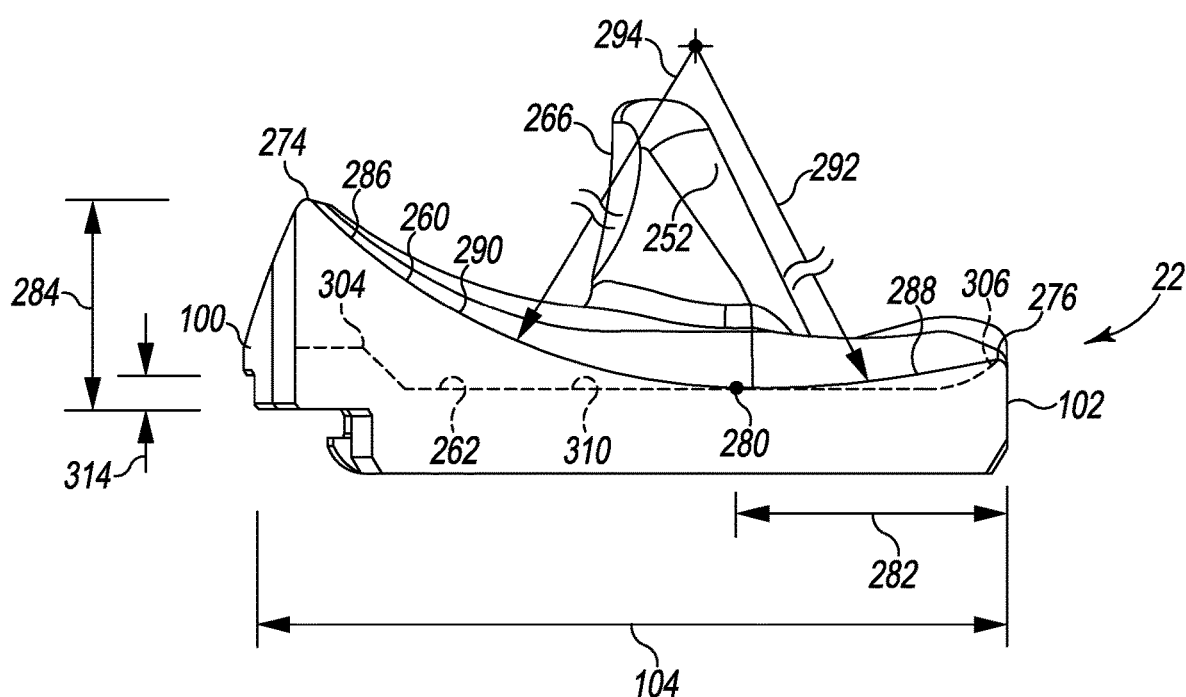
FIG. 7 is a cross-sectional view showing one of the tibial tray insert of FIG. 6 in a sagittal plane along the line 7-7 in FIG. 6.

The surfaces 260, 262 of the tray insert 22 are asymmetrical with the lateral concave surface 262 generally flatter than the medial concave surface 260. The medial surface 260 extends from an anterior edge 274 to a posterior edge 276 within the anterior and posterior ends 100, 102 of the insert 22. As shown in FIG. 7, the medial surface 260 has a distal-most point 280 positioned between the edges 274, 276. An anterior-posterior distance 282 is defined between the distal-most point 280 and the posterior end 102 of the insert 22. In the illustrative embodiment, the anterior-posterior distance 282 is less than the corresponding anterior-posterior distance 122 of either of the surfaces 110, 112 of the tibial tray insert 18 such that the distal-most point 280 of the medial surface 260 is more posterior than the distal-most point 120 of each of the surfaces 110, 112. In the illustrative embodiment, the position of the distal-most point 280 of the medial surface 260 as a percentage of the total length of insert 22 (i.e., the percentage ratio between the anterior-posterior distance 282 and the anterior-posterior distance 104) is in a range of 36% to 39% in the illustrative embodiment.

In some embodiments, the percentage ratio may be based on an anterior-posterior distance measured from the anterior edge of the tibial tray when the insert 22 is mounted on the tray. In such embodiments, the percentage ratio between that anterior-posterior distance and the anterior-posterior distance 104 may be in a range of 58% to 60%. In some embodiments, that percentage ratio may be equal to about 59%.

The medial surface 260 of the insert 122 has an anterior height 284 that is defined between the distal-most point 280 and the anterior edge 274 of the medial surface when viewed in a sagittal plane. In the illustrative embodiment, the anterior height 284 is greater than the anterior height 124 of either the medial or lateral surfaces 110, 112 of the insert 18. In the illustrative embodiment, the medial surface 260 defines an arc 286 that extends between the anterior edge 274 and the posterior edge 276 when it is viewed in the sagittal plane. The arc 286 includes a plurality of arc sections 288, including an anterior arc section 290 extending from the anterior edge 274. Each arc section 288 has a radius of curvature 292. In the illustrative embodiment, the radius of curvature of the anterior arc section 290 (hereinafter radius 294) is smaller than the radius of curvature of the corresponding anterior arc section 130 of the symmetrical CR tray insert 18.

As described above, the lateral surface 262 of insert 22 is generally flatter than the medial surface 260. In the illustrative embodiment, it is also flatter than either of the surfaces 110, 112 of the insert 18. The lateral surface 262 extends from an anterior edge 304 to a posterior edge 306 within the ends 100, 102 of the insert 22. As shown in FIG. 7, the lateral surface 262 has a distal-most section 310 that defines a substantially straight line between the edges 304, 306 and also has an anterior height 314 that is defined between the distal-most section 310 and the anterior edge 304 of the lateral surface when the insert 22 is viewed in a sagittal plane. In the illustrative embodiment, the anterior height 314 is in a range of 1.3 to 1.5 millimeters.

The configuration of the medial concave surface 260 of the AS tray insert 22 provides additional conformity with the medial condyle of the femoral component 14 at extension. That additional conformity, combined with the asymmetry between the concave surfaces 260, 262 and the engagement of the cam and spine, assists in providing anterior stabilization of the knee at extension in the absence of the ACL. In the illustrative embodiment, capability of the other tray inserts 18, 20 to also interface with the tibial tray 16 provides the surgeon with the option of using any of the tray inserts 18, 20, 22, allowing the surgeon to have greater options in selecting the implant configuration appropriate to the patient's needs.

Figure 8:
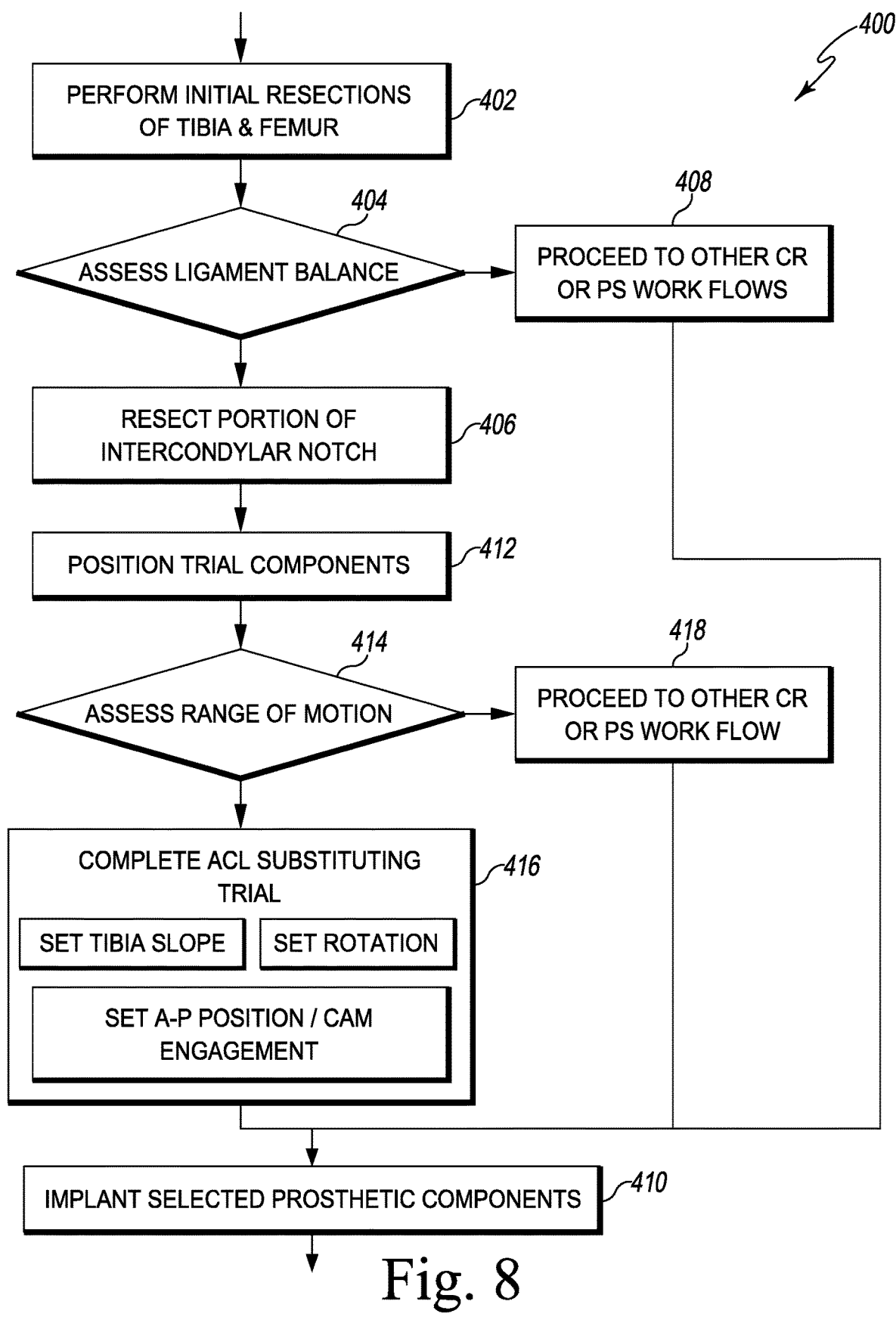
FIG. 8 is a simplified diagram illustrating an orthopaedic surgical method.

Referring now to FIG. 8, a method 400 of performing an orthopaedic surgical procedure on a patient's knee is shown. It should be appreciated that the orthopaedic surgical procedure may include additional steps prior or subsequent to the steps shown in FIG. 8. Additionally, each step shown in FIG. 8 and described in this application may include additional activities not described herein for the purposes of brevity. Some of the activities described in regard to each step may also be varied or modified in ways foreseeable to someone skilled in the art.

Figure 9:
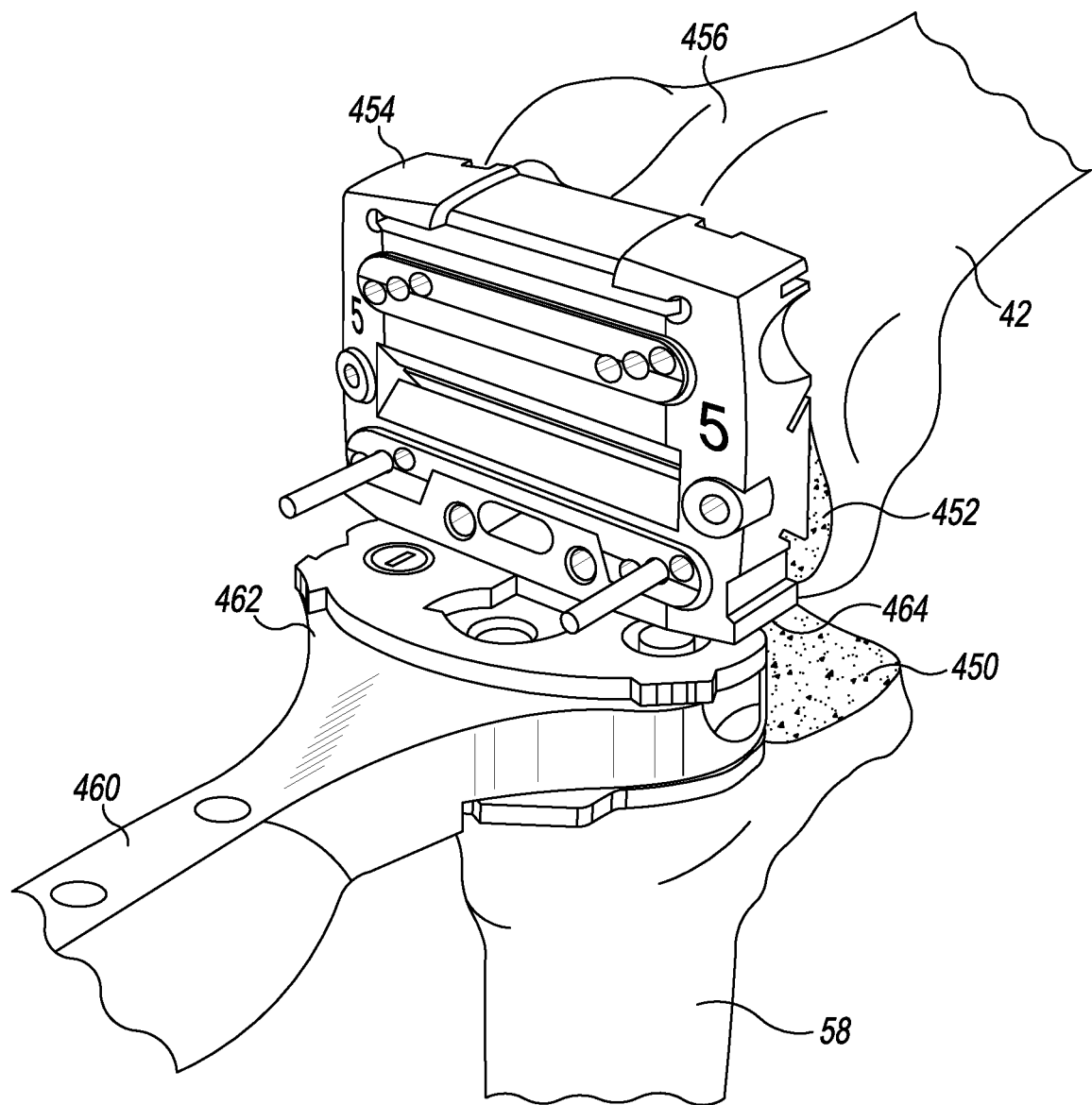
FIG. 9 is an exemplary view showing a step of the orthopaedic surgical method of FIG. 8.

The method 400 includes step or block 402 in which a surgeon or other appropriate individual utilizes various surgical instruments to identify appropriate cutting planes, place cutting blocks, and perform initial resections of a patient's femur 42 and tibia 58. As shown in FIG. 9, the initial resections may create a substantially planar proximal surface 450 on the patient's tibia 58 and a substantially planar distal surface 452 on the patient's femur 42. A multi-cut cutting block, such as, for example, the 4-in-1 cutting block 454 shown in FIG. 9, may also be attached to the planar distal surface 452 such that further resections may be performed prior to the method advancing to block 404. Alternatively, the block 454 may be positioned on the planar distal surface 452 and the activities of block 404 performed before further resections are performed. In still other embodiments, the surgeon may assess the ligament balance and/or assess the range of motion prior to performing any resections.

In block 404, the surgeon may position a spacer instrument 460 in the gap between the patient's femur 42 and tibia 58 to assess the balance of the patient's ligaments. To do so, the surgeon may engage the end 462 of the spacer instrument with the planar proximal surface 450 on the patient's tibia 58 and a distal surface 464 of the 4-in-1 cutting block 454, thereby tensioning the ligaments while the knee is in flexion. In this way, the surgeon may assess the state of the patient's ligaments and the flexion space. As described above, in other embodiments, the surgeon may assess the ligament balance and/or assess the range of motion prior to performing any resections. To assess the range of motion as well as the ligament balance, the surgeon may position the end 462 of the spacer instrument 460 in the gap between the patient's femur 42 and tibia 58 while pivoting the patient's leg over a range of flexion, including, in some cases, full extension and full flexion or hyper-flexion.

Depending on the state of patient's joint, the method 400 may continue to block 406 in which a resection of the intercondylar notch is performed, or to block 408 in which the surgery moves to other cruciate-retaining (CR) or posterior-stabilized (PS) implant workflows in which the patient's bones are prepared to receive prosthetic components in block 410, as described in greater detail below. It should also be appreciated that the initial assessment performed in block 404 may be omitted, and the surgeon may begin with block 406 or with a CR trial reduction similar to that shown and described in U.S. Pat. No. 10,195,056, which is expressly incorporated herein by reference.

In block 406, the surgeon may perform a resection of the patient's intercondylar notch to create a region sized to accommodate the spine 252 of the tray insert 22 and the anterior cam 250 of the femoral component 14. In one embodiment, the surgeon may utilize a cutting guide block 500 (see FIG. 10) to perform the resection. The cutting guide block 500 includes a body 502 shaped to engage the planar distal surface 452 and the anterior portion 456 of the distal end of the patient's femur 42, and a cutting guide slot 504 sized and shaped to guide a cutting blade (not shown) to resect the patient's femur. In the illustrative embodiment, the body 502 includes markings that indicate the anterior geometries of the femoral components 12, 14 (including corresponding left or right leg configurations), and the cutting guide block 500 is configured to permit the surgeon or other user to adjust the cutting guide slot 504 between a position 506 for use on a right femur (see FIG. 11) and a position 508 for use on a left femur (see FIG. 11). It should be appreciated that in other embodiments the system may include a dedicated left femur cutting guide and a dedicated right femur cutting guide. In still other embodiments, the slot may be sized to be usable on the left or right femur.

Figure 10:
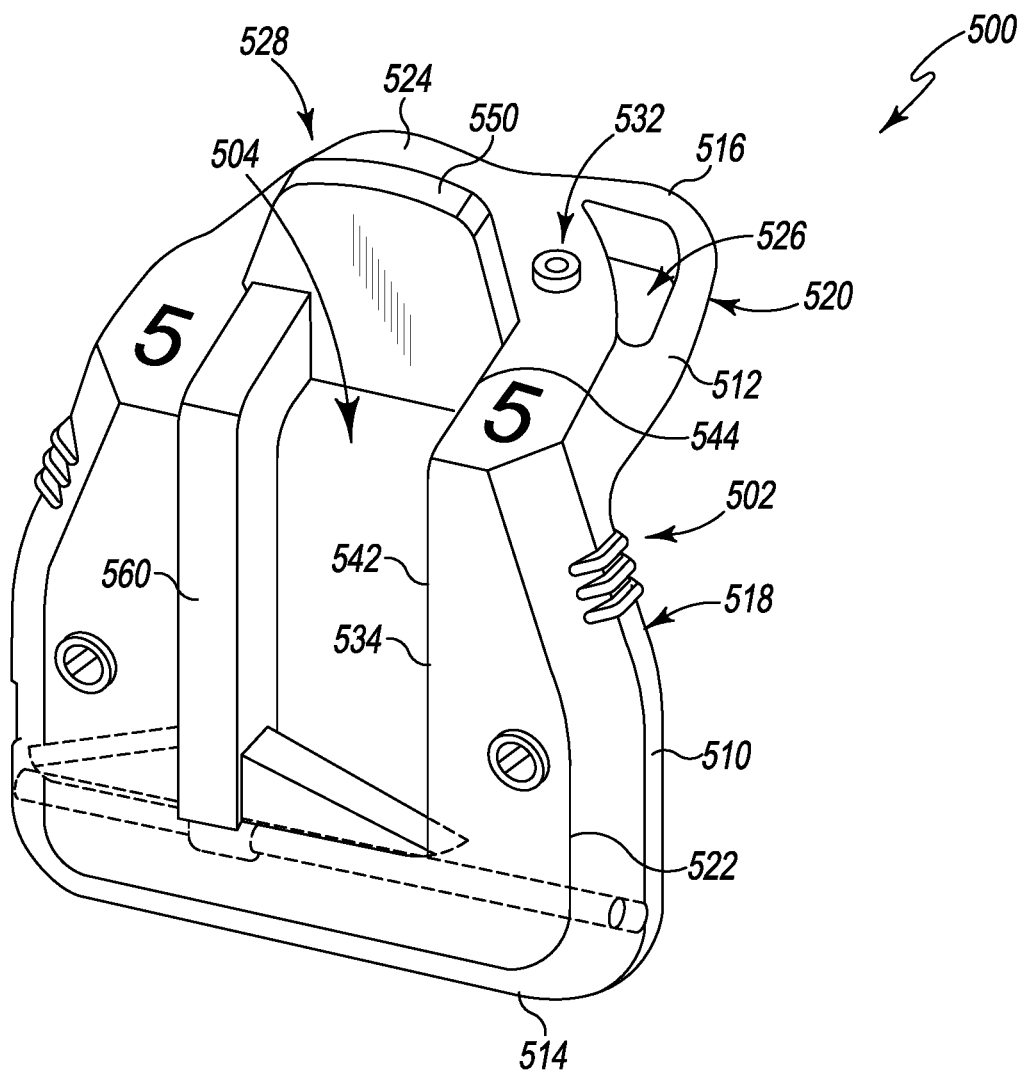
FIG. 10 is a perspective view of a cutting guide block for use in the orthopaedic surgical method of FIG. 8.

As shown in FIG. 10, the body 502 includes a distal plate 510 that extends from an anterior plate 512 to a posterior end 514. The anterior plate 512 extends from its junction with the distal plate 510 to a proximal end 516 such that the body 502 is generally L-shaped when viewed in profile. The plates 510, 512 include bone-facing surfaces 518, 520, respectively, and outer surfaces 522, 524, respectively, which are positioned generally opposite their corresponding bone-facing surfaces. In the illustrative embodiment, the body 502 is formed from a metallic material such as, for example, stainless steel.

The anterior plate 512 includes a pair of viewing ports 526, 528 (see FIG. 13) sized to permit the surgeon to view the area of the patient's bone underlying the plate 512. These ports 526, 528 extend through the outer and bone-facing surfaces of the anterior plate and are shaped and positioned to create representations of the medial and lateral aspects of the femoral component geometry. The surgeon may use those representations to check the position of the cutting guide block 500 on the bone prior to securing the block 500 to the bone with one or more fixation pins 530 (see FIG. 13). The anterior plate 512 illustratively includes a pair of fixation pin guide holes 532, each of which is sized to receive a fixation pin 530.

Figure 12:
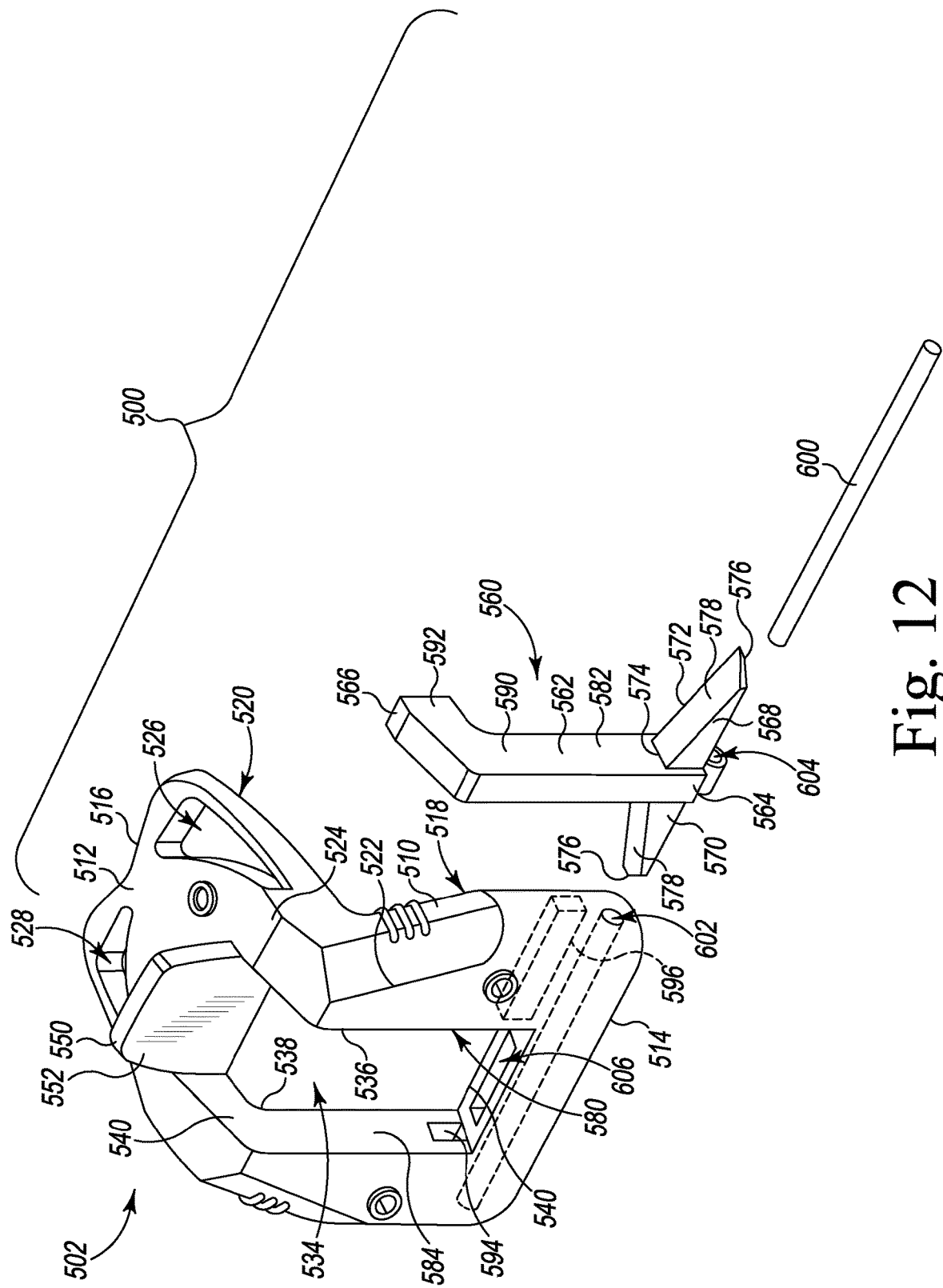
FIG. 12 is an exploded perspective view of the cutting guide block of FIG. 10.

An elongated slot 534 extends through the bone-facing surfaces 518, 520 and the outer surfaces 522, 524 of the distal plate 510 and the anterior plate 512. As shown in FIG. 12, the slot 534 extends from an opening 536 defined in the outer surfaces 522, 524 through an opening 538 defined in the bone-facing surfaces 518, 520 (see FIG. 12). A number of inner walls 540 extend between the openings 536, 538 to define the slot 534. The slot 534 has a distal section 542 and an anterior section 544 such that it is generally L-shaped when viewed in profile.

The cutting guide block 500 also includes a flange 550 that extends outwardly from the anterior plate 512. The flange 550 includes a cutting guide surface 552 that extends into the slot 534 as shown in FIG. 12. In that way, the flange 550 provides an additional support surface for use by the surgeon during the resection. It should be appreciated that similar support flanges may be added to the distal plate 510 at the opposite end of the elongated slot 534.

Figure 11:
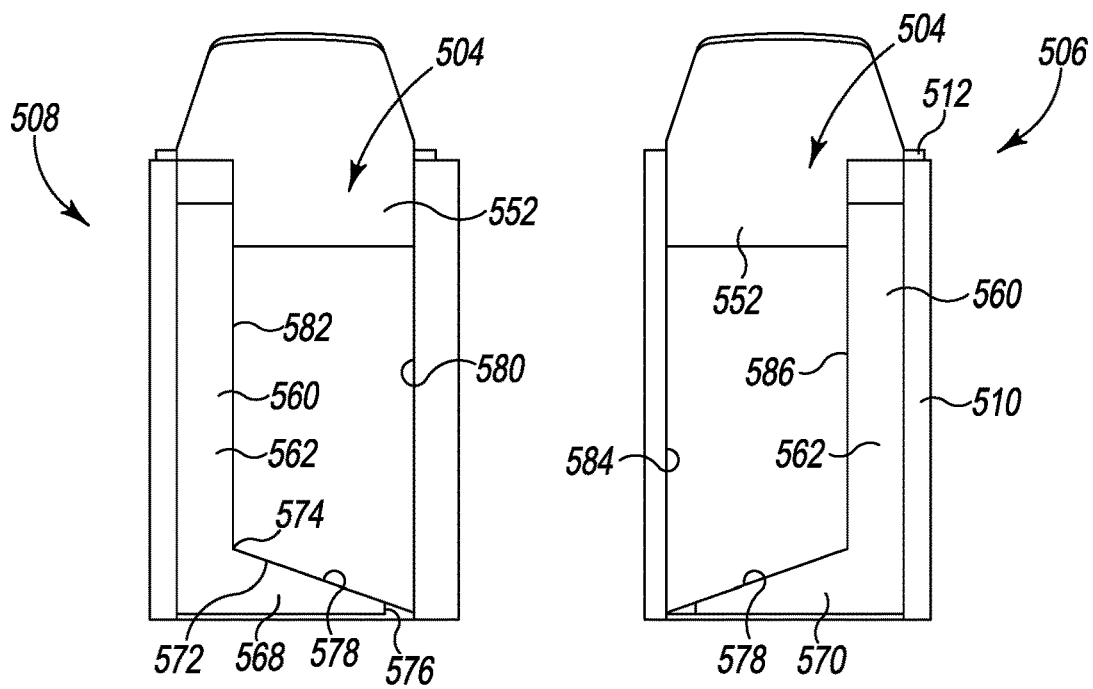
FIG. 11 includes elevation views showing an adjustable body of the cutting guide block of FIG. 10 in different positions.

As described above, the cutting guide slot 504 is adjustable to be repositioned and sized for use on a right femur or a left femur. In the illustrative embodiment, the cutting guide block 500 includes an adjustable body 560 that is configured to be repositioned within the elongated slot 534 to adjust the size and position of the cutting guide slot 504. As shown in FIG. 11, the adjustable body 560 is configured to move relative to the anterior plate 512 and the distal plate 510 between the positions 506, 508 to position the guide slot 504 for use on the right or left femur.

In the illustrative embodiment, the body 560 is formed from a metallic material such as, for example, stainless steel. As shown in FIG. 12, the adjustable body 560 includes a beam 562 that extends from a posterior end 564 to an anterior end 566. A pair of legs 568, 570 extends from the posterior end 564 in opposite directions. In the illustrative embodiment, the configuration of the leg 570 is identical to the configuration of leg 568 such that only leg 568 will be described in detail here for the purposes of brevity. The leg 568 includes an inner wall 572 that extends from an edge 574 attached to the beam 562. The wall 572 extends to a tip 576 and includes a surface 578 that is sloped because the edge 574 is positioned anterior of the tip 576. When the adjustable body 560 is placed at position 508 as shown in FIG. 11, the surface 578 of the leg 568 cooperates with the exposed surfaces 552, 580 of the plates 510, 512 and the exposed surface 582 of the beam 562 to define the cutting guide slot 504 at that position.

When the adjustable body 560 is placed at position 506 as shown in FIG. 11, the surface 578 of the leg 570 cooperates with the exposed surfaces 552, 584 of the plates 510, 512 and the exposed surface 586 of the beam 562 to define the cutting guide slot 504 at that position. The sloped surfaces 578 of the legs 568, 570 (as well as the bodies of the legs) are each sized to assist the surgeon in resecting the patient's femur and to protect the posterior-cruciate ligament (PCL) of the patient during resection. It should be appreciated that in other embodiments one or both of the legs may be omitted.

The surfaces 582, 584 of the beam 562 are positioned on an elongated arm 590 that extends from the posterior end 564 and an anterior arm 592 that extends from the arm 590, as shown in FIG. 12. The arms 590, 592 cooperate to define a medial cutting guide surface of the block 500 when the adjustable body 560 is located at either position 506 or position 508, while one of the legs 568, 570 defines the posterior cutting guide surface. When the body 560 is located at the position 506, the leg 568 is positioned in a pocket or passageway 596 that is defined in the surface 580 of the distal plate 510. When the body 560 is located at the position 508, the leg 570 is positioned in a pocket or passageway 594 that is defined in the surface 584 of the distal plate 510. It should be appreciated that the cutting guide block may include one or more features to prevent inadvertent movement of the adjustable body with the slot.

To facilitate movement of the adjustable body 560, the cutting guide block 500 includes a cylindrical rod 600 that is secured within the distal plate 510 in a passageway 602. The adjustable body 560 includes an eyelet 604 that is positioned below the posterior end 564 of the beam 562 and is sized to receive the rod 600. In the illustrative embodiment, the distal plate 510 includes a channel 606 that opens into the elongated slot 534 and the passageway 602. The channel 606 is sized to receive the eyelet 604 and permit the eyelet 604 (and hence the adjustable body 560) to be moved between the positions 506, 508. It should be appreciated that in other embodiments the adjustable body may be detachable from the rest of the cutting guide block 500 to reposition the cutting guide slot.

Figure 13:
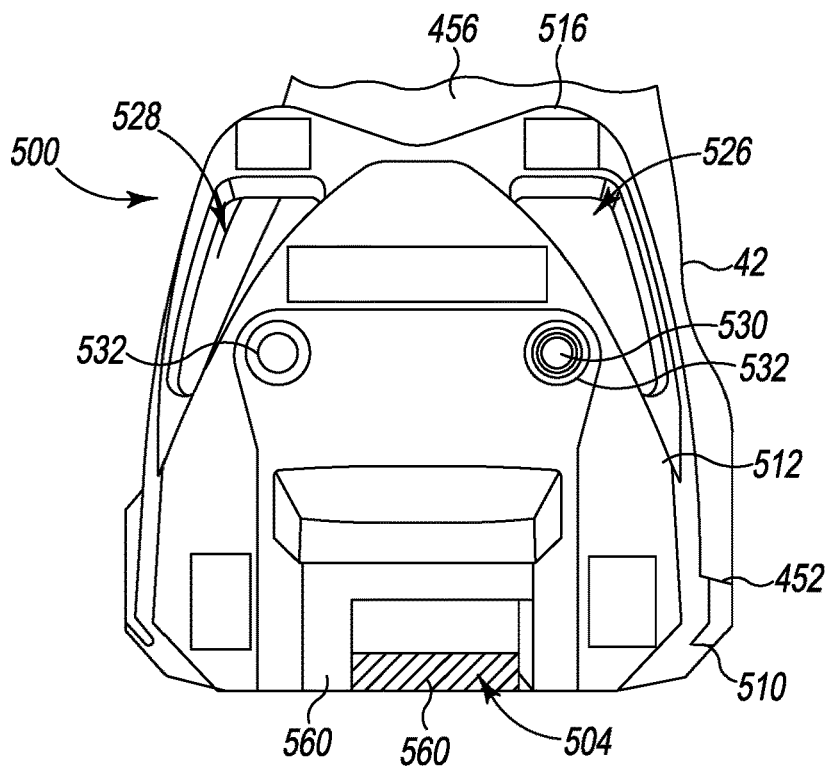
FIG. 13 is an exemplary view showing a step of the orthopaedic surgical method of FIG. 8 utilizing the cutting guide block of FIG. 10.

Returning to the method 400, the surgeon may perform the resection of the patient's intercondylar notch utilizing the cutting guide block 500. As shown in FIG. 13, the surgeon may position the cutting guide block 500 on the patient's femur. In the illustrative embodiment, the patient's femur is a left femur, so the adjustable body 560 is positioned in the position 508. At the position 508, the longitudinal axis of the cutting guide slot 504 is offset from the longitudinal axis of the guide block, and the slot is aligned with the portions of the patient's femur 42 that are to be resected to accommodate the spine 252 of the tray insert 22 and the anterior cam 250 of the femoral component 14. As described above, the leg 568 of the adjustable body 560 is positioned with respect to the patient's PCL to protect it during resection. The surgeon may then utilize a cutting saw blade to resect the intercondylar notch. The method 400 may advance to block 412 after the resection(s) is complete.

In block 412, the surgeon may select trial components for use in, for example, a trial reduction process in which the range of motion is assessed to determine the type and configuration of each of the various types of prosthetic components to be implanted. In the illustrative embodiment, the surgeon may select trial components corresponding to the femoral component 14 and the tibial tray insert 22, which include the anterior cam 250 and spine 252, respectively. It should be appreciated that even after the resection performed in block 406, the surgeon may select trial components associated with the femoral component 12 and the tray inserts 18, 20 and choose to implant those components as appropriate for the needs of the particular patient.

Figure 14:
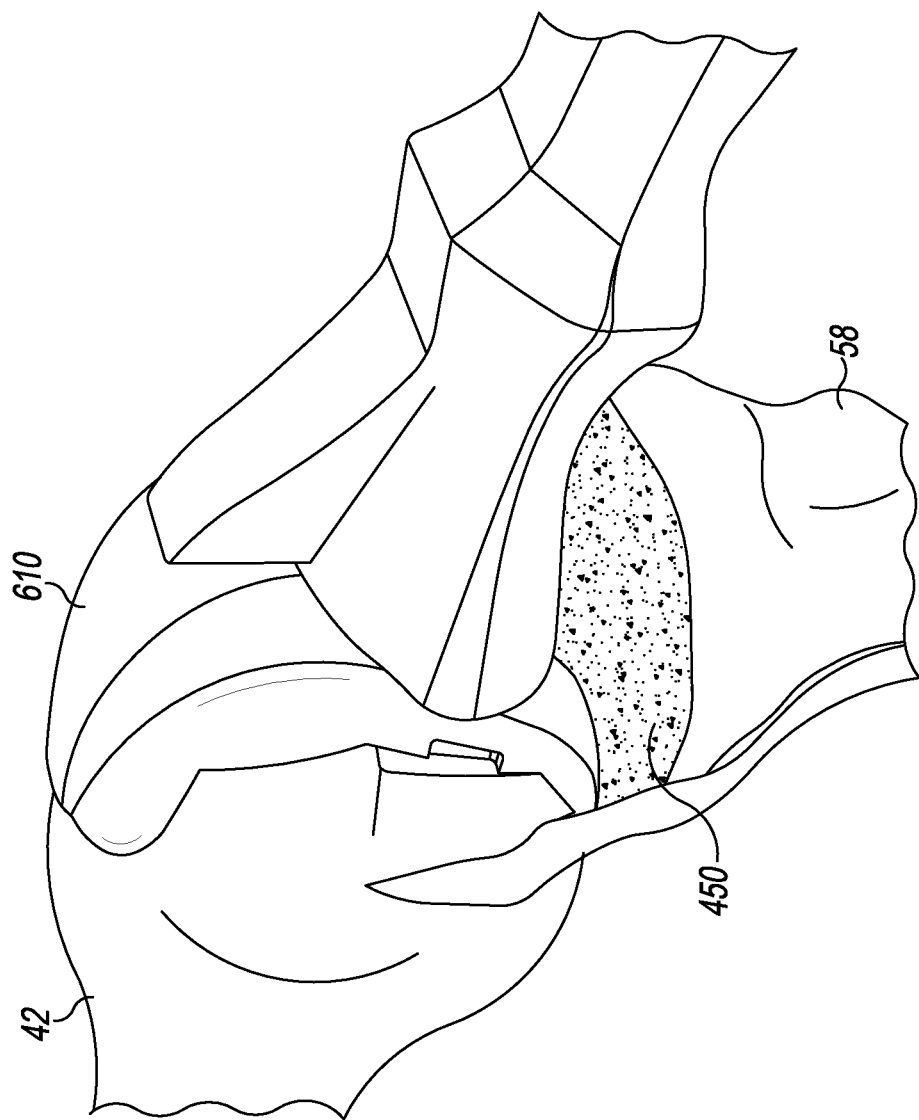
FIG. 14 is an exemplary view showing another step of the orthopaedic surgical method of FIG. 8.

As shown in FIG. 14, when the surgeon has selected a femoral prosthetic trial component 610, which illustratively corresponds to the femoral component 14, the surgeon may position it on the distal end of the patient's femur 42 after resecting the anterior surface, posterior surface, and chamfer surfaces of the patient's femur. In other embodiments, the surgeon may utilize a femoral trial component similar to that shown and described in U.S. patent application Ser. No. 16/458,077 entitled "FEMORAL TRIAL COMPONENTS AND ASSOCIATED ORTHOPAEDIC SURGICAL METHOD OF USE," which is expressly incorporated herein by reference. In such embodiments, some or all of blocks 412, 414, 416 may be performed before the resection of anterior surface, posterior surface, and chamfer surfaces of the patient's femur.

Figure 15:
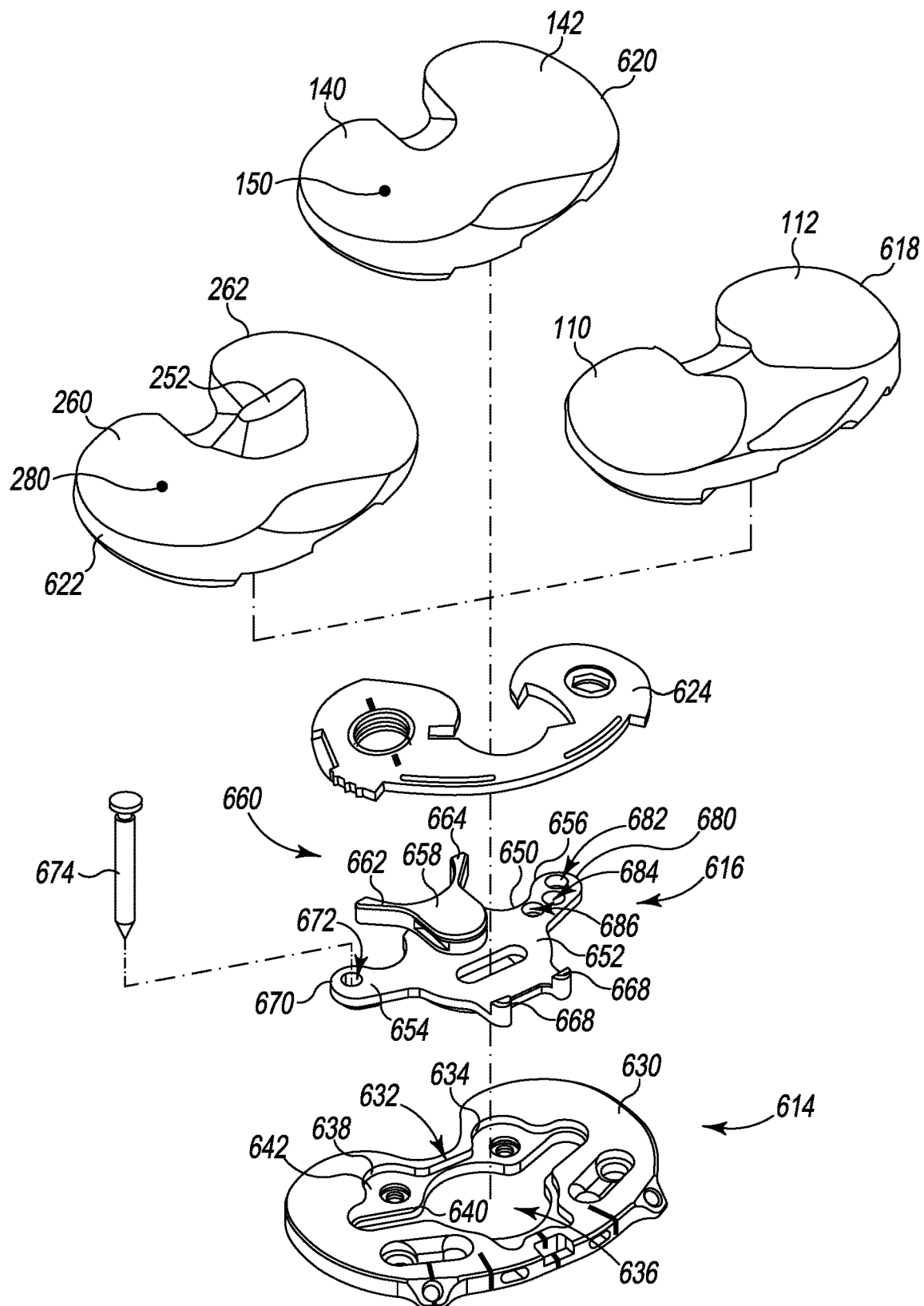
FIG. 15 is an exploded perspective view of various trial components for use in the orthopaedic surgical method of FIG. 8.

The surgeon may also select tibial trial components. Referring now to FIG. 15, the tibial trial components include a tibial base trial component 614, an evaluation component 616, and a number of tibial surface trial components 618, 620, 622, which correspond to the tibial tray inserts 18, 20, 22, respectively. In the illustrative embodiment, each surface trial component is configured to be separately coupled to a shim 624 (or to no shim) to form a tibial insert trial component, which permits the surgeon to selectively adjust the overall height of the trial construct depending on the state of the patient's bony anatomy and ligaments. Each assembled tibial insert trial component may be attached to the evaluation component 616 and the base trial component 614 during the trial reduction. Exemplary embodiments of the shims, the base trial component, and their method of use are shown and described in U.S. Pat. No. 10,195,056, which is expressly incorporated herein by reference. It should be appreciated that in other embodiments the tibial insert trial components may be monolithic/solid components with the shims and surface trials combined into a single component.

In the illustrative embodiment, the tibial surface trial component 622 includes a spine 252 and bearing surfaces 260, 262 corresponding to the tray insert 22 described above. The surgeon may therefore select the trial component 622, attach it to the shim 624, and attach the shim 624 and trial component 622 to the components 614, 616 for trial reduction with the femoral trial component 610, as described in greater detail below.

The surface trial components 618, 620, 622 are illustratively formed from a polymeric material such as, for example, polyethylene or other plastic materials. The shims are formed from a combination of polymeric materials and metallic materials, such as, for example, polyethylene and stainless steel. The tibial base trial and evaluations components are illustratively formed from metallic materials such as, for example, stainless steel.

The tibial base trial component 614 may be attached to the proximal end of the patient's tibia. It should be appreciated that the tibial base trial component 614, like the other trial components, may be formed in a number of different sizes to accommodate bones of various sizes. As shown in FIG. 15, the tibial base trial component 614 includes a plate 630 that has a central opening 632. An inner wall 634 extends downwardly from the central opening 632 to define a passageway 636 through the plate 630. The inner wall 634 includes an upper wall 638 and a lower wall 640 that is offset or otherwise spaced inwardly from the upper wall 638. The upper wall 638 and the lower wall 640 cooperate to define a shelf surface 642 positioned between the inferior surface and the superior surface of the plate. As will be discussed in greater detail below, the configuration of the passageway 636 permits the advancement of various surgical drills, punches, and other instruments into the proximal end of the patient's tibia.

As shown in FIG. 15, the tibial evaluation component 616 is configured to be positioned in the passageway 636 of the tibial base trial component 614 to form a tibial tray trial component. In the illustrative embodiment, the tibial evaluation component 616 has a base plate 650 having a central platform 652 and a pair of prongs 654, 656 that extend outwardly from the central platform 652. A post 658, which is part of a posterior buttress 660, extends upwardly from the central platform 652. The posterior buttress 660 also includes a pair of arms 662, 664 that extend posteriorly from the post 658 to cantilevered tips. The tibial evaluation component 616 also includes an anterior buttress 668 positioned opposite the posterior buttress. In the illustrative embodiment, the buttresses 660, 668 are configured to separately engage each tibial insert/bearing trial component assembly (i.e., formed by surface trial components 618, 620, or 622 and a shim 624).

The prong 654 extends medially from the central platform 652 to an outer tip 670. A through-hole 672, which is sized to receive a fixation pin 674, extends through the prong near the outer tip 670. The fixation pin 674 is sized to extend through the hole 672 to engage the patient's bone. In the illustrative embodiment, the through-hole 672 is positioned to align with the distal-most point 280 of the medial concave surface 260 of the insert trial 622. In other words, the center of the through-hole 672 is positioned on an imaginary line extending in an inferior-superior direction through the distal-most point 280 when the insert trial 622 is coupled to the evaluation component 616. As a result, the fixation pin 674, when it extends through the hole 672 into the patient's bone, is also positioned on the same imaginary line, and an axis of rotation is defined by the pin 674 about which the tibial evaluation component 616 (and hence the tibial insert trial component assembly and tibial base trial component 614) are permitted to rotate, as described in greater detail below.

The other prong 656 extends laterally from the central platform 652 to an outer tip 680. In the illustrative embodiment, a plurality of through-holes 682, 684, 686 extend through the prong 656. Each of the through-holes 682, 684, 686 is sized to receive a fixation pin 674. When fixation pins are positioned in the through-hole 672 of the prong 654 and any of the through-holes 682, 684, 686 of the prong 656, the tibial evaluation component 616 (and hence the tibial insert trial component assembly and tibial base trial component 614) are prevented from rotating relative to the patient's tibia.

Figure 16:
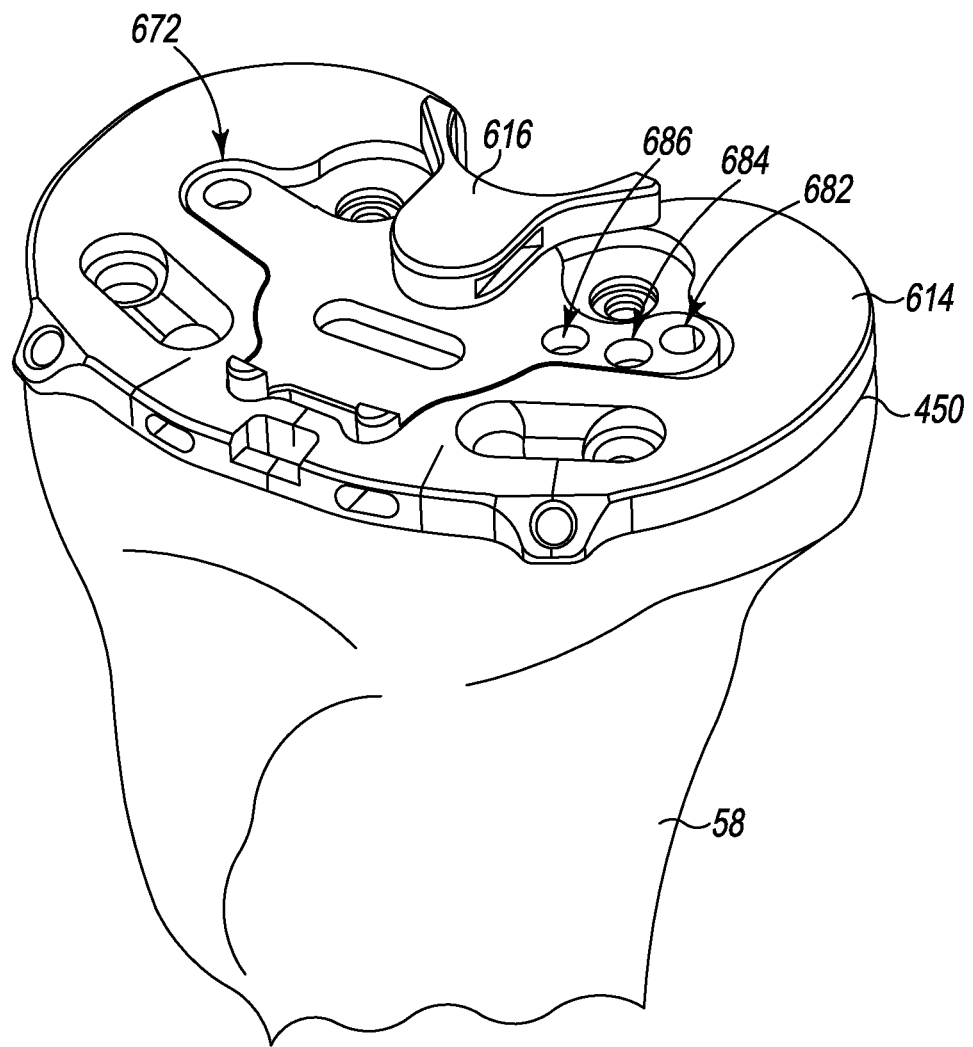
FIGS. 16-19 are exemplary views showing other steps of the orthopaedic surgical method of FIG. 8 utilizing various trial components of FIG. 15.

The trial components are selected in block 412 of the method 400 of FIG. 8 for use in a trial reduction process. As shown in FIG. 8, the method 400 may advance to block 414 in which the trial reduction process, including an assessment of the range of motion, is performed. The surgeon may begin by placing the tibial base trial component 614 on the patient's tibia, as shown in FIG. 16. The surgeon may also insert the evaluation component 616 into the base trial 614 and a fixation pin 674 into the medial through-hole 672 of the prong 654. The insert trial 622 and a shim 624 may be attached to the evaluation component 616 over the head of the fixation pin 674 to form a tibial trial construct 688 as shown in FIG. 17.

As described above, the fixation pin 674, when it extends through the hole 672 into the patient's bone, is positioned on an imaginary line extending in an inferior-superior direction, which extends through the distal-most point 280 of the insert trial 622 when the insert trial 622 and a shim 624 is coupled to the evaluation component 616. The position of the through-hole 672 should also be aligned to the Medial Collateral Ligament (MCL) in the anterior-posterior direction to near the anterior-posterior center of the MCL insertions into the proximal tibial. The medial-lateral position with respect to the MCL is determined based on tibial base size and coverage relative to the resected proximal tibia.

Figure 17:
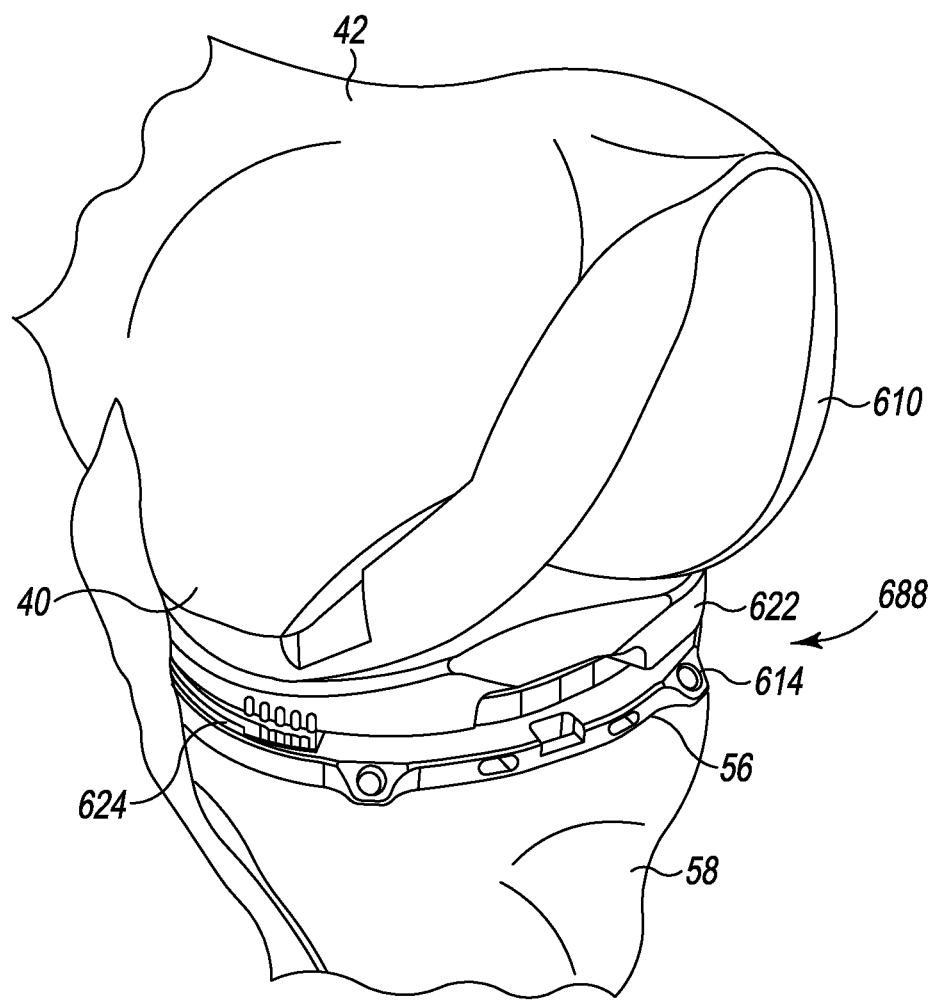
Figure 18:
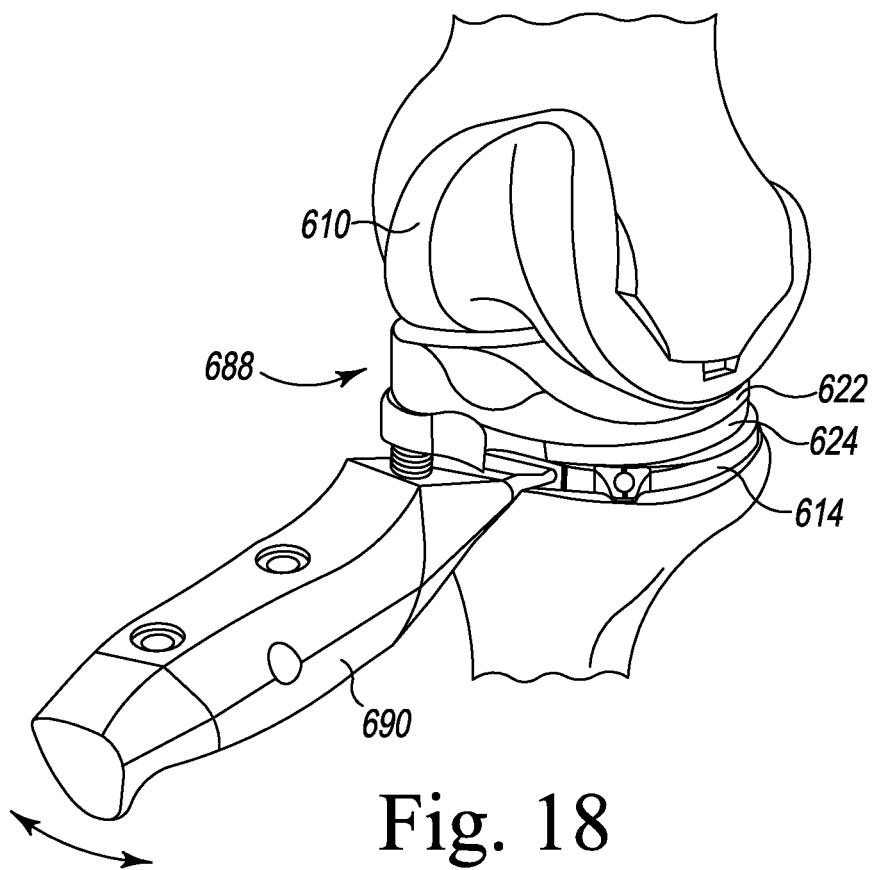
Figure 19:
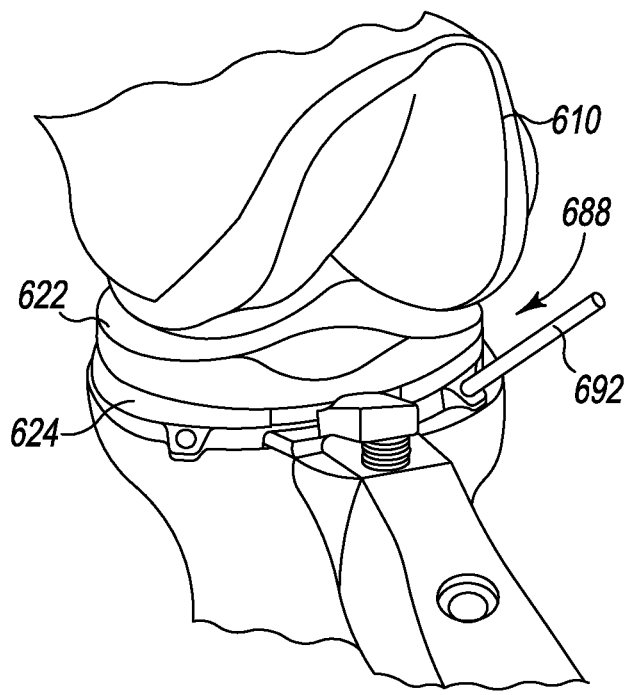

To evaluate the range of motion, the surgeon may place the leg in extension, as shown in FIG. 17. The surgeon may also attach a surgical handle 690 (see FIG. 18) to the front of the base trial 614 to control the rotation of the tibial trial construct 688 about the fixation pin 674. The surgeon may also choose to hold the tibial trial construct 688 in position by hand. In still other embodiments, the surgeon may place the trial construct at a particular rotational position on the tibia and use one of the lateral through-holes 682, 684, 686 to temporarily lock the trial construct at that position. The surgeon may then move the leg between early flexion and full extension, evaluating the range of motion and the cam/post interaction between the femoral trial 610 and the tibial trial construct 688. The surgeon may move the trial construct to other rotational positions on the patient's tibia to locate the position providing appropriate engagement between the cam and post, as well as acceptable tibial rotation relative to the femur. The surgeon may also assess the tension of the PCL. If the surgeon determines the trial construct is in the correct position/rotation, the surgeon may pin construct in place through one of the anterior holes of the tray 614.

Based on these factors, the surgeon may proceed to block 416 to continue the trialing process for the ACL-Substituting prosthesis formed by the femoral component 14 and the tibial insert 22 or proceed to block 418 in which the surgeon proceeds to other cruciate-retaining (CR) or posterior-stabilized (PS) implant workflows. In block 418, the surgeon may prepare the patient's bones to receive other prosthetic components, including the tray inserts 18, 20 and the femoral component 12. It should be appreciated that if the surgeon proceeds to block 418, the surgeon may utilize the tibial base trial component 614, tibial evaluation component 616, and any desired size of shim 624 if further trial reduction is required. In the illustrative embodiment, each of the surface trials 618, 620 are configured to separately couple to a shim 624 to form insert trial assemblies corresponding to the tray inserts 18, 20, respectively.

If the surgeon proceeds to block 416 to continue the trialing process for the femoral component 14, the surgeon may continue assessing the range of motion to set the final rotational position of the tibial trial construct 688. To do so, the surgeon may select the rotational position providing appropriate engagement between the cam and post, as well as acceptable tibial rotation relative to the femur. The surgeon may also pick the final position based the tension of the ligaments. When the construct is in the desired rotational position, the surgeon may advance a fixation pin 692 through an anterior fixation hole of the tibial base trial component 614 to secure the tibial trial construct 688 in the desired position.

Figure 20:
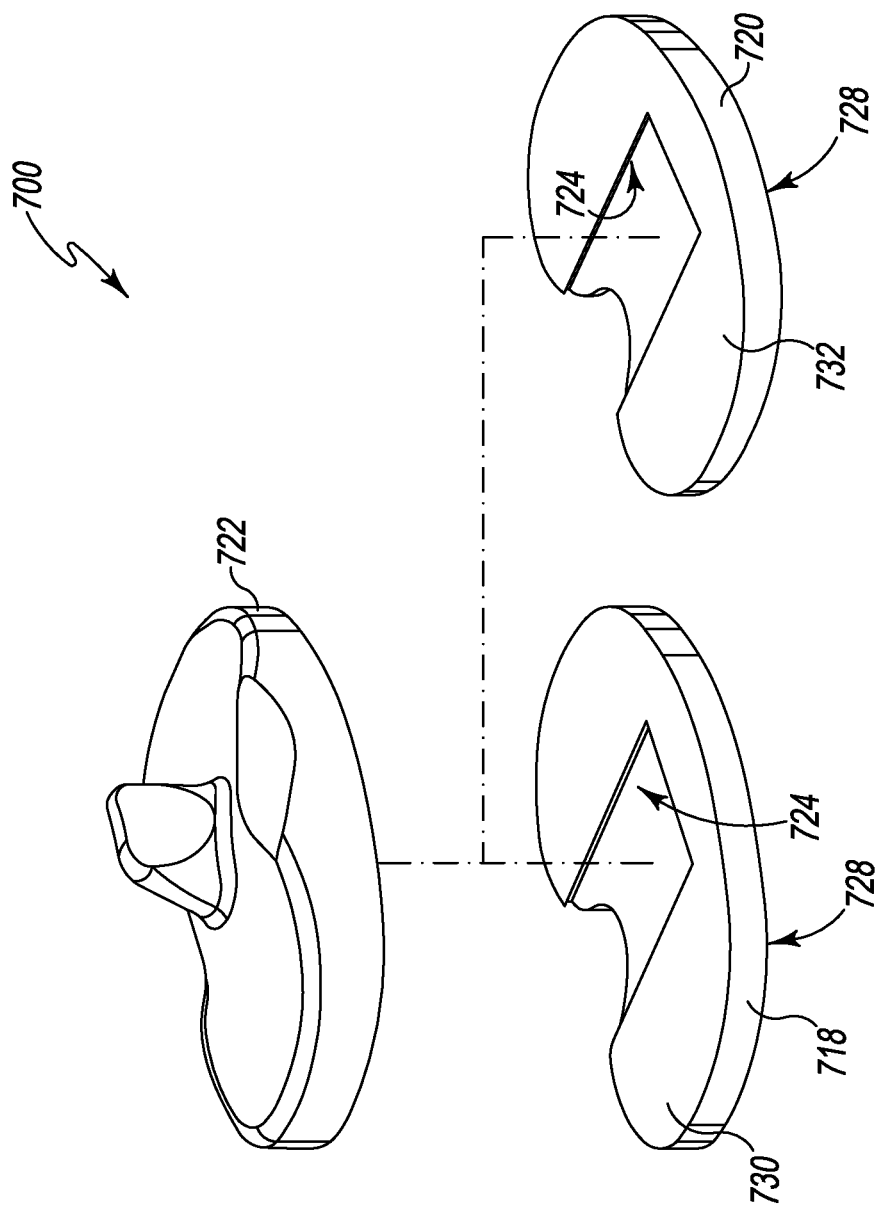
FIG. 20 is an exploded perspective view of slope trial components for use in the orthopaedic surgical method of FIG. 8.

As shown in FIG. 8, the surgeon may also set tibial slope in block 416. To do so, the surgeon may utilize the slope trial system 700 shown in FIGS. 20-22. The system 700 includes a plurality of shim bases 718, 720 configured to be separately coupled to a tibial surface trial 722 corresponding to the configuration of the tibial tray insert 22. In the illustrative embodiment, each base includes a groove 724 that is configured to engage a corresponding flange 726 (see FIG. 21) of the trial 722. The flange and groove form a dovetail joint in the illustrative embodiment to removably secure the trial to the base.

Figure 21:
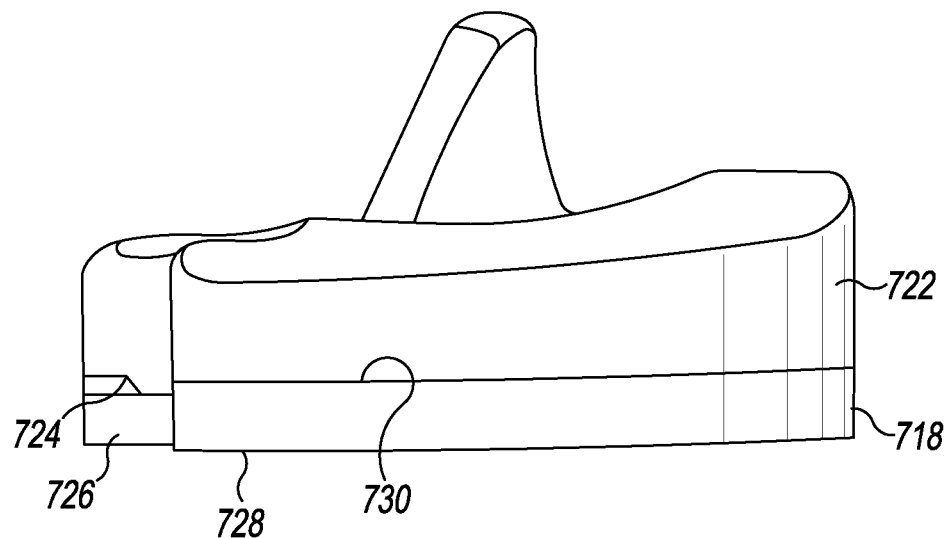
FIGS. 21-22 are elevation views of the slope trial components of FIG. 20.
Figure 22:
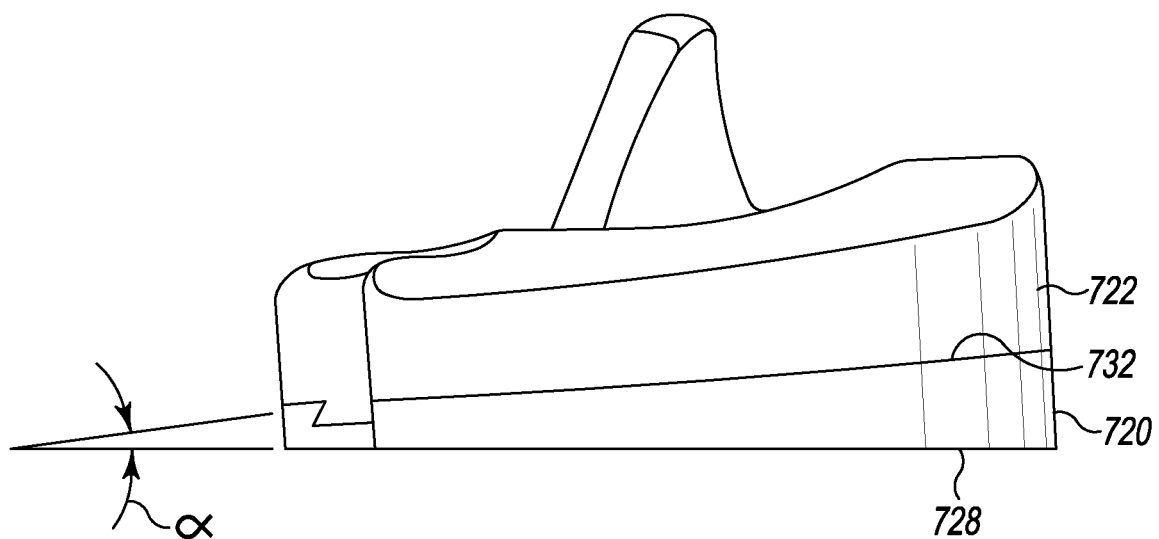

Each base includes a distal surface 728 configured to engage a resected proximal surface of the patient's tibia and an opposite facing proximal surface. As shown in FIG. 21, the proximal surface 730 of the base 718 extends generally parallel to the distal surface 728 such that no tilt or slope is imparted to the surface trial 722. As shown in FIG. 22, the proximal surface 732 of the base 720 is angled relative to the distal surface 726. In the illustrative embodiment, the angle α defined between the surfaces 726, 730 is equal to 3 degrees such that a three degree slope is imparted to the surface trial 722 when it is attached to the base 720. It should be appreciated that although only two bases with two slope options are shown, the system 700 may include additional bases having proximal surfaces angled at other degrees relative to the corresponding distal surfaces. The angle α may be in a range of −5 degrees to +10 degrees. In some embodiments, the angle α may be equal to 0, 2, or 4 degrees.

Although shown without any means of securing the bases to the patient's bone, in other embodiments each base may include spikes or any number of through-holes sized to receive fixation pins to selectively secure the bases to the patient's tibia while the slope is evaluated. When a trial construct including the trial 722 and one of the bases 718, 720 is assembled and placed on the tibia, assessment of the cam/post engagement and range of motion may be evaluated at various slopes by inserting different bases. Once the desired slope is identified, a tibial re-cut block (not shown) may be attached to the patient bone, and the final resection performed to add the selected slope. It should be appreciated that in other embodiments the trial constructs including trials 718, 720, or 722 may be mounted to the tray base trial 614.

As described above, the surgeon may also utilize a femoral trial component similar to that shown and described in U.S. patent application Ser. No. 16/458,077 entitled "FEMORAL TRIAL COMPONENTS AND ASSOCIATED ORTHOPAEDIC SURGICAL METHOD OF USE," which is expressly incorporated herein by reference. In such embodiments, the surgeon may perform a final check of the proposed anterior-posterior engagement of the cam and post in block 416 in conjunction with setting tibial rotation and tibial slope. In still other embodiments, the surgeon may utilize the tibial base trial system and associated instrumentation shown and described in U.S. Prov. Appl. No. 62/898, 237 entitled "ADJUSTABLE TIBIAL TRIAL INSTRUMENT AND ORTHOPAEDIC SURGICAL METHOD OF USING THE SAME", which is expressly incorporated herein by reference.

Figure 23:
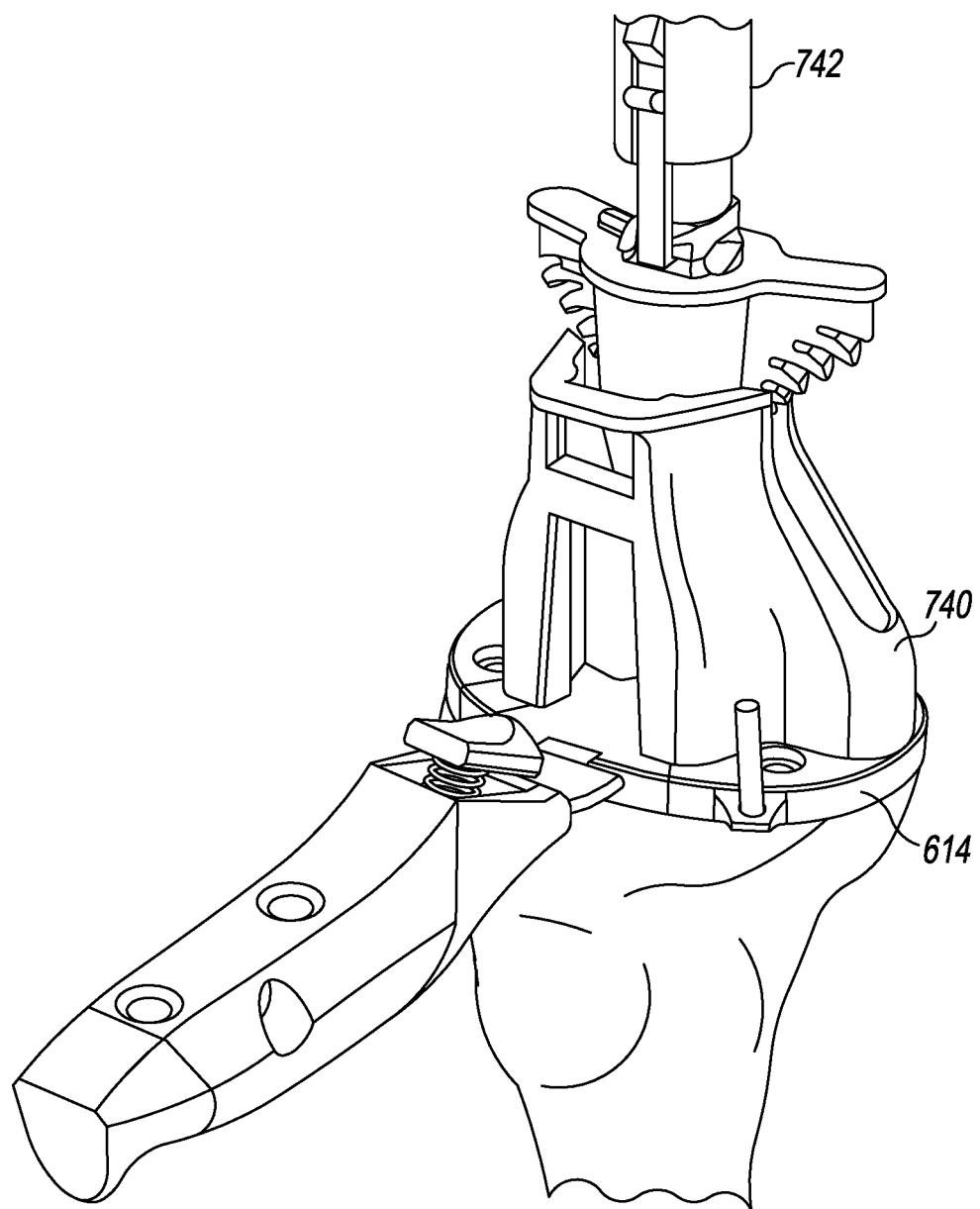
FIG. 23 is an exemplary view of another step of the orthopaedic surgical method of FIG. 8.

After completing blocks 408, 416, or 418 of the method 400, the surgeon may continue the surgical preparation of the patient's tibia and femur in manner similar to that described in, for example, U.S. Pat. No. 10,195,056, which is hereby incorporated by reference. For example, as shown in FIG. 23, the surgeon may remove the evaluation component 616 after securing the tibial base trial 614 to patient's tibia using additional fixation pins. The surgeon may attach the guide tower 740 to the base trial 614 to guide the insertion of additional tools, including, for example, a broach 742, to continue the preparation of the bone. When the bone preparation is complete, the surgeon may implant the selected components of the system 10 in block 410.

Referring now to FIGS. 24-28, another system 800 of tibial trial components is shown. The system 800, like the tibial trial components described above in regard to FIG. 15, may be utilized to trial and select a set of implant components, including, in particular, a femoral component 14, a tibial tray insert 22, and a tibial tray 16. The system 800 includes a tibial base trial component 802 configured to be attached to the proximal end of the patient's tibia, an evaluation component 804 configured to be coupled to the base trial component 802, and a tibial bearing/insert trial component 806 configured to be attached to the other components 802, 804. The tibial insert trial component 806 includes medial and lateral concave surfaces 808, 810 and a post 812 corresponding to corresponding features of a tibial tray insert. The post and surfaces are configured to engage with an anterior cam and corresponding condyle surfaces of a femoral trial component or of a femoral prosthetic component. The materials used in components 802, 804, 806 are similar to those described above in regard to components 614, 616, 622, respectively.

Figure 24:
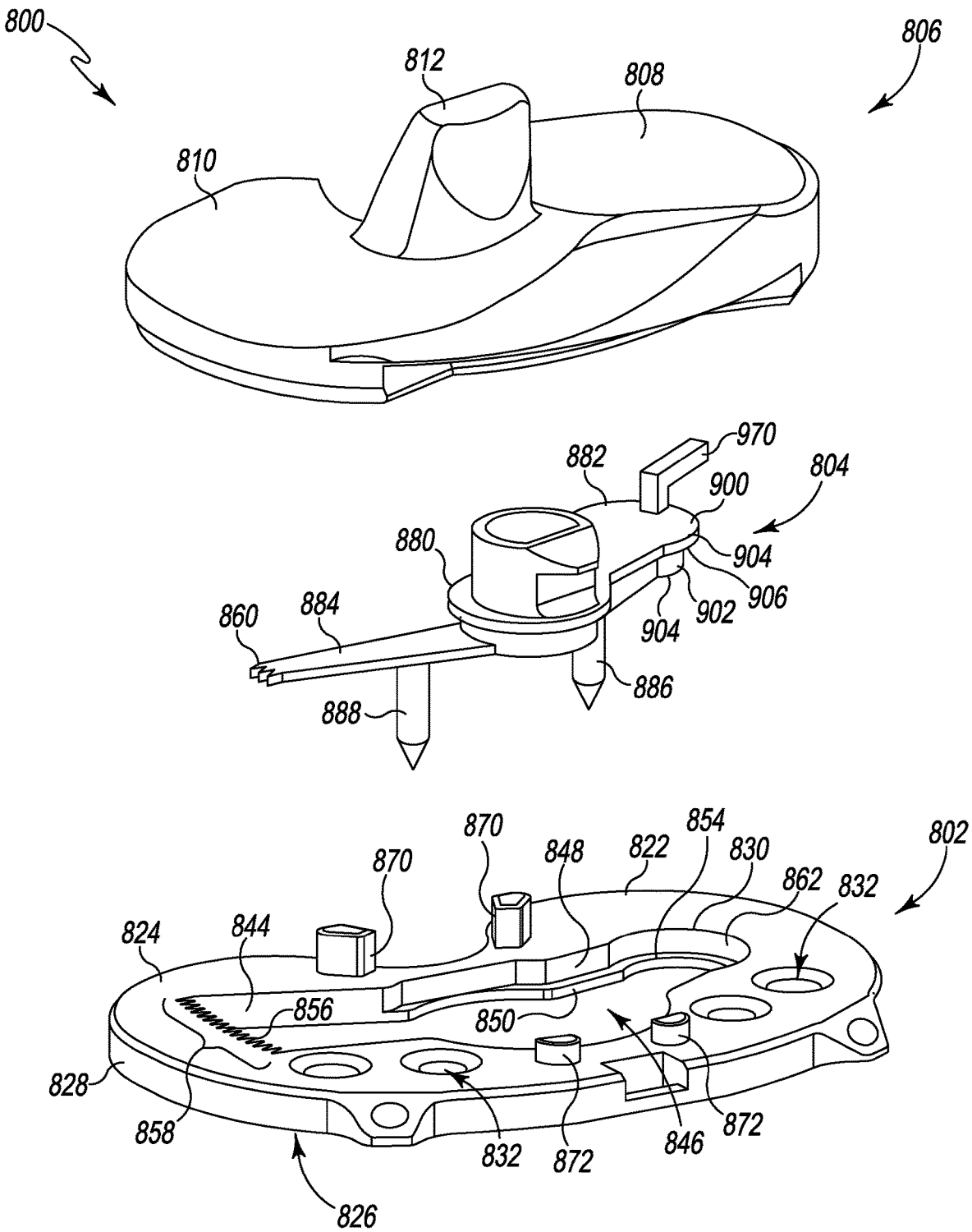
FIG. 24 is an exploded perspective view of a system of trial components.
Figure 25:
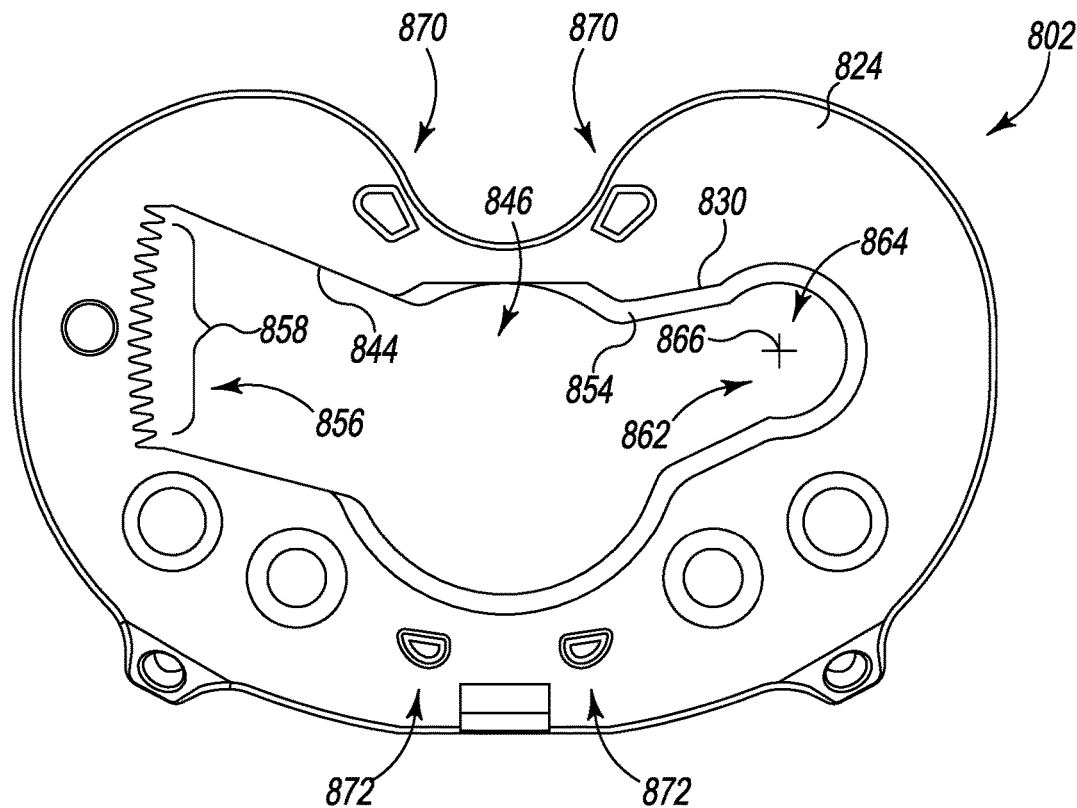
FIG. 25 is a plan view of the tibial base trial component of the system of FIG. 24.
Figure 26:
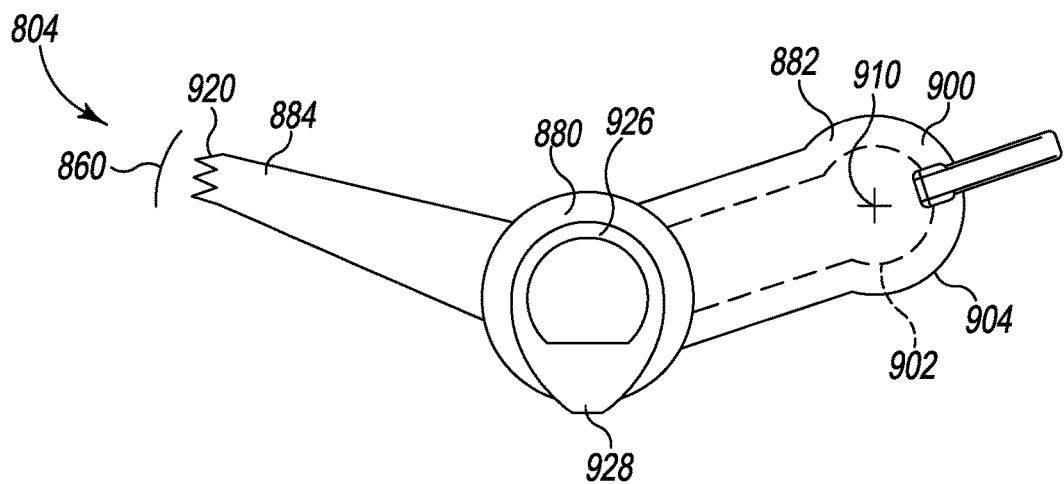
FIG. 26 is a plan view of the evaluation trial component of the system of FIG. 24.

As shown in FIGS. 24-25, the tibial base trial component 802 includes a plate 822 having a superior surface 824, an inferior surface 826, and an outer sidewall 828 extending between the surfaces 824, 826. The plate 822 includes a plate opening 830 defined in the superior surface 824. A number of through holes 832, which are configured to receive fixation pins or spikes of a drill tower (not shown), extend through the surfaces 824, 826. An inner wall 844 extends downwardly from the plate opening 830 to define a passageway 846 through the plate 822. The inner wall 844 includes an upper wall 848 and a lower wall 850 that is offset or otherwise spaced inwardly from the upper wall 848. The upper wall 848 and the lower wall 850 cooperate to define a shelf surface 854 positioned between the inferior surface 826 and the superior surface 824.

The inner wall 844 includes a lateral section 856 that defines a concave arc. The lateral section 856 includes a first portion of a locking mechanism in the form a plurality of teeth 858 defined on the lateral section and face into the passageway 846. As described in greater detail below, the teeth 858 are configured to engage a second portion of the locking mechanism (i.e., corresponding teeth 860) of the evaluation component 804 to prevent relative rotation between the evaluation component 804 and the tibial base trial component 802. As shown in FIG. 25, the inner wall 844 also includes a medial section 862 that defines a partially cylindrical section 864 of the passageway 846. The section 864 has a central axis 866 about which the evaluation component 804 or the tibial base trial component 802 may rotate relative to the other component when the teeth 858, 860 are not engaged, as described in greater detail below.

The tibial base trial component 802 includes a posterior buttress 870 and an anterior buttress 872 configured to engage the tibial insert trial component 806 to prevent relative movement between the components 802, 806. In the illustrative embodiment, the buttresses 870, 872 each include a pair of posts extending upwardly from the superior surface 824. In other embodiments, the buttresses may include other structures configured to prevent relative movement.

The evaluation component 804 includes a central platform 880 and a pair of prongs 882, 884 that extend outwardly from the central platform 880. In the illustrative embodiment, a pair of spikes 886, 888 extend downwardly from the prongs 882, 884, respectively. Each spike is configured to engage the patient's tibia to temporarily attach the evaluation component 804 to the patient's tibia.

The prong 882 is a medial prong that includes a medial tip 900 configured to be received in the partially cylindrical section 864 of the passageway 846 of the tibial base trial component 802. The medial tip 900 includes a body 902 extending from an inferior end 904. The body 902 is configured to confront the lower wall 850 of the tibial base trial component 802. The medial tip 900 also includes a flange 904 that extends outwardly at the superior end 906 of the body 902 to confront the upper wall 848. In the illustrative embodiment, the body 902 has a central axis 910 (see FIG. 26) that is coincident with the central axis 866 of the base trial 802 when the components are coupled together.

The prong 884 is a lateral prong that includes a lateral tip 920. In the illustratively embodiment, the lateral tip 920 includes the second portion of the locking mechanism in the form of the plurality of teeth 860, which are configured to engage the teeth 858 of the tibial base trial component 802. As shown in FIG. 24, the prong 884 (and hence the teeth 860) are positioned inferiorly of the flange 904 of the medial tip 900.

The evaluation component 804 also includes a post 926 extends upwardly from the central platform 880. In the illustrative embodiment, the post 926 includes a connector 928 that is formed in its superior end. The connector 928 is configured to receive a locking flange associated with an impaction or extraction handle (now shown).

Figure 27:
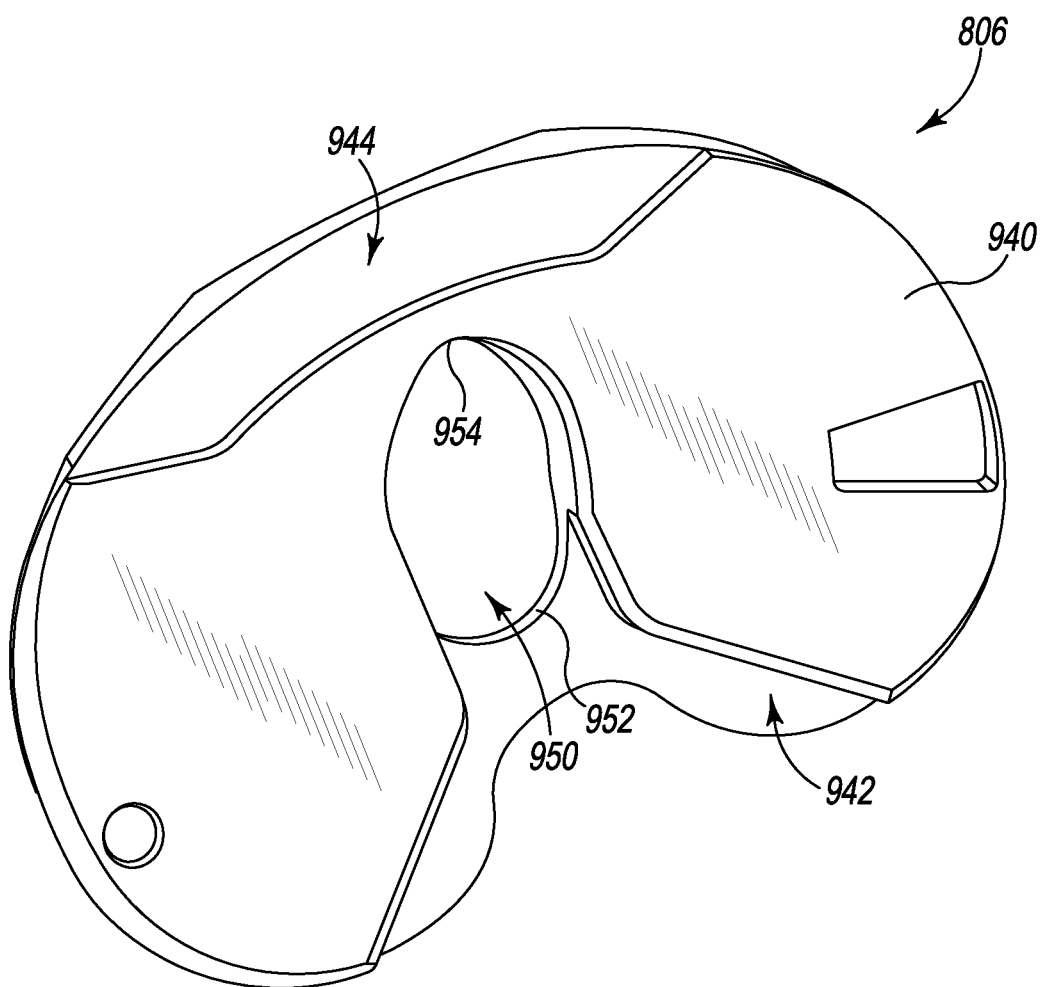
FIG. 27 is a perspective view of the tibial insert trial component of the system of FIG. 24.

Referring now to FIG. 27, the tibial insert trial component 806 includes a distal surface 940 configured to engage the tibial base trial component 802. A posterior channel 942 is defined in the distal surface 940. The channel is sized and shaped to receive the posterior buttress 870 of the tibial base trial component 802. The tibial insert trial component 806 also includes an anterior channel 944 that is sized and shaped to receive the anterior buttress 872 of the base trial 802 of the tibial tray 16. The walls defining the channels 942, 944 cooperate with the buttresses 870, 872 to prevent relative rotation between the base trial 802 and the insert trial 806.

The insert trial 806 also includes a slot 950 sized and shaped to receive the post 926 of the evaluation component 804. In the illustrative embodiment, the slot 950 is elongated and extends from a posterior end 952 to an anterior end 954. The slot 950 is curved such that when the base trial 802 and the insert trial 806 are pivoted relative to the evaluation component 804, the slot defines a curved channel that moves around the post 926.

Figure 28:
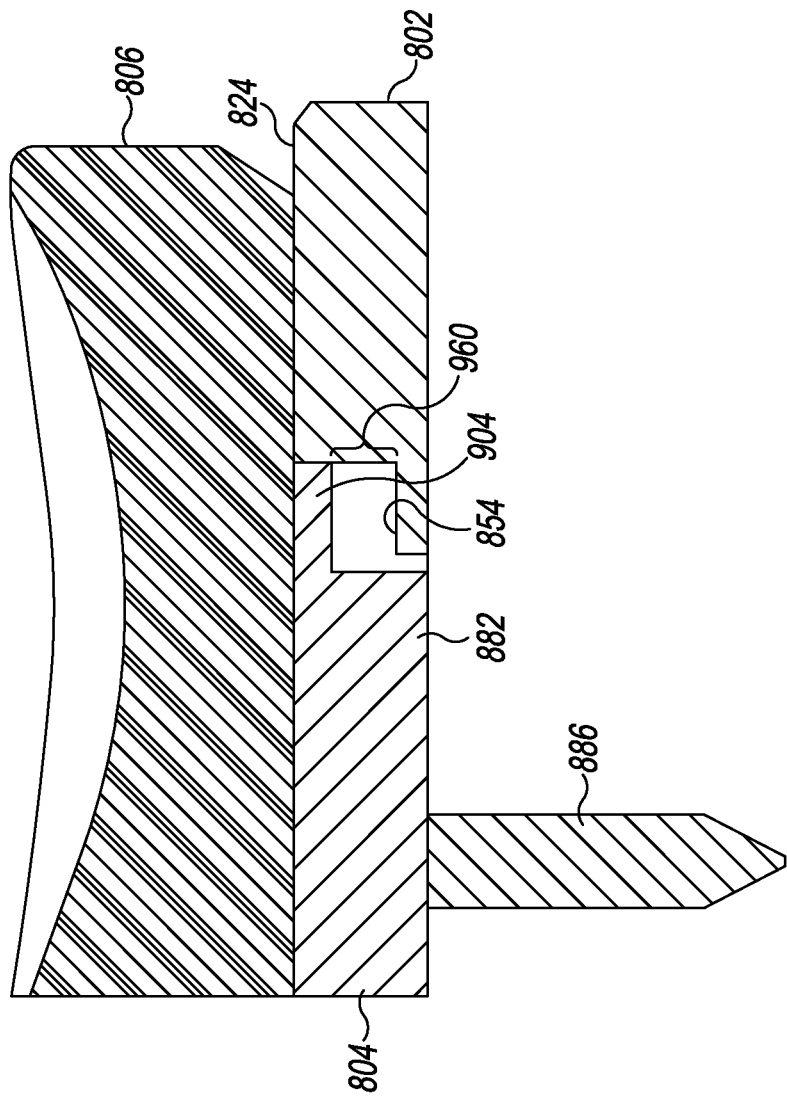
FIG. 28 is a cross-sectional view of a portion of the system of FIG. 24.

In use, the evaluation component 804 is positioned in the passageway 846 of the base trial 802 such that the spikes 886, 888 may extend into the patient's bone and the teeth 858 are interdigitated with the teeth 860. The insert trial 806 is positioned over the post 926 of the evaluation component 804 between the buttresses 870, 872. In the illustrative embodiment, the distal-most point of the medial concave surface of the insert trial 806 is positioned on the central axis 866 of the base trial 802, and, as shown in FIG. 28, the insert trial 806 engages the superior surface 824 of the base trial 802. The superior flange 904 of the medial prong 882 of the evaluation component 804 is spaced apart from the shelf surface 854 of the base trial 802 such that a gap 960 is defined between them.

The surgeon may change the rotational position of the base trial 802 (and hence the insert trial 806) on the patient's tibia. To do so, the surgeon may lift the base trial 802 and the insert trial 806 off of the bone to disengage the teeth 858 from the teeth 860. The position of the flange 904 relative to the shelf surface 854 limits the amount the surgeon may lift the base trial 802. With the teeth 858, 860 disengaged, the surgeon may rotate the base trial 802 and the insert trial 806 relative to the patient's tibia (and hence evaluation component 804) about the central axis 866 to another rotational position. The surgeon may then lower the base trial 802 back to engagement with the patient's tibia, reengaging the teeth 858, 860 to lock the base trial 802 into that position.

After selecting the final rotational position, the surgeon may continue the surgical preparation of the patient's tibia and femur in a manner similar to that described above. For example, the surgeon may remove the evaluation component 804 after securing the tibial base trial 802 to patient's tibia using additional fixation pins. The surgeon may attach the guide tower 740 to the base trial 802 to guide the insertion of additional tools, including, for example, a broach 742, to continue the preparation of the bone. In the illustrative embodiment, the component 804 includes an arm 970 (see FIG. 24) that prevents the surgeon from attaching the guide tower 740 to the base trial 802 while the component 804 is engaged with the base trial.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument, comprising:
an anterior plate configured to engage an anterior surface of a patient's femur,
a distal plate attached to, and extending from, the anterior plate to a posterior end, the distal plate being configured to engage a distal surface of the patient's femur,
wherein the orthopaedic surgical instrument includes a notch cutting guide slot defined by a plurality of inner walls, wherein the anterior plate includes a first inner wall of the plurality of inner walls, the first inner wall having a distal cutting guide surface configured to guide a resection of a distal portion of an intercondylar notch of the patient's femur to resize the intercondylar notch to receive a cam of a femoral component, and wherein the plurality of inner walls includes a second inner wall having a posterior cutting guide surface configured to guide a resection of a posterior portion of the intercondylar notch of the patient's femur, the posterior cutting guide surface being configured to support a cutting blade and including a first edge and a second edge, wherein the posterior cutting guide has a constant slope from the first edge to the second edge such that the first edge is positioned more anterior than the second edge to protect a posterior-cruciate ligament (PCL) of the patient during resection.

2. The orthopaedic surgical instrument of claim 1, further comprising:

an adjustable body configured to move relative to the anterior plate and the distal plate to change the configuration of the notch cutting guide slot, wherein the adjustable body includes the second inner wall.

3. The orthopaedic surgical instrument of claim 2, wherein the adjustable body includes a third inner wall extending in a direction opposite the second inner wall, the third inner wall having a posterior cutting guide surface configured to guide a resection of a posterior portion of an intercondylar notch of a patient's other femur, the posterior cutting guide surface including a first edge and a second edge and being sloped such that the first edge of the third inner wall is positioned more anterior than the second edge of the third inner wall to protect a posterior-cruciate ligament (PCL) connected to the patient's other femur during resection.

4. The orthopaedic surgical instrument of claim 3, wherein the adjustable body is operable to slide relative to the anterior plate and the distal plate between a first position in which the second inner wall defines a portion of the notch cutting guide slot and a second position in which the third inner wall defines a portion of the notch cutting guide slot.

5. The orthopaedic surgical instrument of claim 4, wherein:

the distal plate includes a first passageway and a second passageway positioned opposite the first passageway, and the third inner wall is sized to be positioned in the first passageway when the adjustable body is in the first position, and the second inner wall is sized to be positioned in the second passageway when the adjustable body is in the second position.

6. The orthopaedic surgical instrument of claim 2, wherein the adjustable body includes a first arm extending anteriorly from the second inner wall and a second arm extending proximally from the first arm, the first arm and the second arm including a medial cutting guide surface configured to guide a resection of a medial side of the intercondylar notch of the patient's femur.

7. The orthopaedic surgical instrument of claim 1, wherein:

a central axis of the orthopaedic surgical instrument extends in an anterior-posterior direction through the anterior plate when the orthopaedic surgical instrument is viewed in a transverse plane, and the notch cutting guide slot has a longitudinal axis that extends parallel to the central axis when the orthopaedic surgical instrument is viewed in a transverse plane, the longitudinal axis being laterally offset from the central axis.

8. An orthopaedic surgical instrument, comprising:

an anterior plate configured to engage an anterior surface of a patient's femur, a distal plate attached to, and extending from, the anterior plate to a posterior end, the distal plate being configured to engage a distal surface of the patient's femur, an elongated slot defined in the anterior plate and the distal plate, and an adjustable body positioned in the elongated slot, wherein the adjustable body cooperates with the anterior plate and the distal plate to define a notch cutting guide slot in the orthopaedic surgical instrument, and wherein the adjustable body includes a first posterior arm having a planar cutting guide configured to support a cutting blade and a second posterior arm extending in a direction opposite the first posterior arm and having a second planar cutting guide configured to support the cutting blade, and the adjustable body is configured to slide relative to the anterior plate and the distal plate between a first position in which the first planar cutting guide cooperates with the anterior plate and the distal plate to define a first notch cutting guide slot and a second position in which the second planar cutting guide cooperates with the anterior plate and the distal plate to define a second notch cutting guide slot.

9. The orthopaedic surgical instrument of claim 8, wherein:

the first notch cutting guide slot is sized and positioned to resect a patient's left femur, and the second notch cutting guide is slot sized and positioned to resect a patient's right femur.

10. The orthopaedic surgical instrument of claim 9, wherein:

the first posterior arm has a first posterior cutting guide surface including a first edge and a second edge, the first posterior cutting guide surface being sloped such that the first edge of the first posterior arm is positioned more anterior than the second edge to protect a posterior-cruciate ligament (PCL) of the patient's left femur when the adjustable body is positioned in the first position, and the second posterior arm has a second posterior cutting guide surface including a third edge and a fourth edge, the second posterior cutting guide surface being sloped such that the third edge of the second posterior arm is positioned more anterior than the fourth edge to protect a posterior-cruciate ligament (PCL) of the patient's right femur when the adjustable body is positioned in the second position.

* * * * *